(12) United States Patent
Ashkenazi et al.

(10) Patent No.: US 6,693,181 B2
(45) Date of Patent: Feb. 17, 2004

(54) PROTEIN SECRETION

(75) Inventors: Avi J. Ashkenazi, San Mateo, CA (US); Phillip W. Berman, Portola Valley, CA (US); David Brousseau, San Francisco, CA (US); Tina Etcheverry, Berkeley, CA (US)

(73) Assignee: Genentech, Inc., S. San Francisco, CA (US)

( * ) Notice: Subject to any disclaimer, the term of this patent is extended or adjusted under 35 U.S.C. 154(b) by 0 days.

(21) Appl. No.: 09/291,925

(22) Filed: Apr. 14, 1999

(65) Prior Publication Data

US 2002/0155525 A1 Oct. 24, 2002

Related U.S. Application Data

(60) Provisional application No. 60/082,002, filed on Apr. 16, 1998, and provisional application No. 60/123,522, filed on Mar. 8, 1999.

(51) Int. Cl.[7] .............................................. C07H 21/04
(52) U.S. Cl. .................... 536/23.4; 536/23.5; 435/69.1; 435/69.8; 435/70.1; 530/350
(58) Field of Search ............................ 435/69.7, 69.5, 435/69.8, 455, 69.1, 70.1; 536/23.5, 23.4; 530/351

(56) References Cited

U.S. PATENT DOCUMENTS

| | | | |
|---|---|---|---|
| 4,766,075 A | 8/1988 | Goeddel et al. |
| 4,795,706 A | 1/1989 | Hsiung et al. |
| 5,037,743 A | 8/1991 | Welch et al. |
| 5,225,537 A | 7/1993 | Foster |
| 5,565,335 A | 10/1996 | Capon et al. |
| 5,614,612 A | 3/1997 | Haigwood et al. |
| 5,641,655 A | 6/1997 | Foster et al. |
| 5,653,985 A | 8/1997 | Haigwood et al. |
| 5,696,238 A | 12/1997 | Haigwood et al. |
| 5,702,938 A | 12/1997 | Goeddel et al. |
| 5,880,268 A | 3/1999 | Gallatin et al. |

FOREIGN PATENT DOCUMENTS

| | | |
|---|---|---|
| EP | 356409 | 2/1990 |
| WO | WO 92/04444 | 3/1992 |
| WO | WO 96/17067 | 6/1996 |

OTHER PUBLICATIONS

Alexander and Elder, "Carbohydrate dramatically influences immune reactivity of antisera to viral glycoprotein antigens" *Science* 226(4680):1328–1330 (Dec. 14, 1984).

Aruffo et al., "CD44 is the Principal Cell Surface Receptor for Hyaluronate" *Cell* 61:1303–1313 (Jun. 29, 1990).

Ashkenazi et al., "Protection Against Endotoxic Shock by a Tumor Necrosis Factor Receptor Immunoadhesin" *Proc. Natl. Acad. Sci.* 88:10535–10539 (1991).

Ashwell and Harford, "Carbohydrate–specific receptors of the liver" *Annual Review of Biochemistry* 51:531–554 (1982).

Ashwell and Morrell, "The role of surface carbohydrates in the hepatic recognition and transport of circulating glycoproteins" *Advances in Enzymology* 41:99–128 (1974).

Bennett et al., "Extracellular Domain–IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060–23067 (Dec. 5, 1991).

Berg and Grinnell, "Signal and propeptide processing of human tissue plasminogen activator: activity of a pro–tPA derivative" *Biochemical and Biophysical Research Communications* 179(3):1289–1296 (Sep. 30, 1991).

Berman et al., "Engineering Glycoproteins for Use as Pharmaceuticals" *Trends in Biotechnology* 3(2):51–53 (Feb. 1985).

Berman et al., "Expression and Immunogenicity of the Extracellular Domain of the Human Immunodeficiency Virus Type 1 Envelope Glycoprotein, gp160" *Journal of Virology* 63(8):3489–3498 (1989).

Byrn et al., "Biological Properties of a CD4 Immunoadhesin" *Nature* 344:667–670 (Apr. 12, 1990).

Capon et al., "Designing CD4 Immunoadhesins for AIDS Therapy" *Nature* 337:525–531 (Feb. 9, 1989).

Caton et al., "The antigenic structure of the influenza virus A/PR/8/34 hemagglutinin (H1 subtype)" *Cell* 31(2 Pt 1):417–427 (Dec. 1982).

Chalupny et al., "T–cell activation molecule 4–1BB binds to extracellular matrix proteins" *Proc. Natl. Acad. Sci. USA* 89(21):10360–10364 (Nov. 1, 1992).

Claffey et al., "Structural requirements for dimerization, glycosylation, and biological function of VPF/VEGF" *Biochimica et Biophysica Acta* 1246(1):1–9 (Jan. 5, 1995).

Collier et al., "Specific glycosylation site mutations of the insulin receptor α subunit impair intracellular transport" *Biochemistry* 32(30):7818–7823 (Aug. 3, 1993).

Culp et al., "Regulated expression allows high level production and secretion of HIV–1 gp120 envelope glycoprotein in *Drosophila Schneider* cells" *Bio/Technology* 9(2):173–177 (Feb. 1991).

(List continued on next page.)

*Primary Examiner*—Lynette R. F. Smith
*Assistant Examiner*—Robert A. Zeman
(74) *Attorney, Agent, or Firm*—Merchant & Gould P.C.

(57) ABSTRACT

DNA constructs, host cells and production methods are disclosed for the expression and recovery of polypeptides, especially those altered to have one or more glycosylation sites added or deleted. The DNA constructs, host cells and methods provided herein employ a DNA segment corresponding to a mammalian tissue plasminogen activator signal and/or pro peptide.

13 Claims, 9 Drawing Sheets

OTHER PUBLICATIONS

Dorner et al., "The relationship of N–linked glycosylation and heavy chain–binding protein association with the secretion of glycoproteins" *Journal of Cell Biology* 105(6 Pt 1):2665–2674 (Dec. 1987).

Dube et al., "Glycosylation at specific sites of erythropoietin is essential for biosynthesis, secretion, and biological function," *Journal of Biological Chemistry* 263(33):17516–17521 (Nov. 25, 1988).

Feng et al., "The structure of the TATA–less rat tissue–type plasminogen activator gene. Species–specific sequence divergences in the promoter predict differences in regulation of gene expression" *Journal of Biological Chemistry* 265(4)::2022–2027 (Feb. 5, 1990).

Fiedler and Simons, "The role of N–glycans in the secretory pathway" *Cell* 81(3):309–312 (May 5, 1995).

Flack et al., "Site–directed mutagenesis defines the individual role of the glycosylation sites on follicle–stimulating hormone" *Journal of Biological Chemistry* 269(19):14015–14020 (May 13, 1994).

Gallagher et al., "Glycosylation requirements for intracellular transport and function of the hemagglutinin of influenza virus" *Journal of Virology* 66(12):7136–7145 (Dec. 1992).

Gray et al., "Cloning of human tumor necrosis factor (TNF) receptor cDNA and expression of recombinant soluble TNF- -binding protein" *Proc. Natl. Acad. Sci. USA* 87(19):7380–7384 (Oct. 1990).

Helenius, A., "How N–linked oligosaccharides affect glycoprotein folding in the endoplasmic reticulum" *Molecular Biology of the Cell* 5(3):253–265 (Mar. 1994).

Kery et al., "Ligand recognition by purified human mannose receptor" *Archives of Biochemistry & Biophysics* 298(1):49–55 (Oct. 1992).

Kohno et al., "A second tumor necrosis factor receptor gene product can shed a naturally occurring tumor necrosis factor inhibitor" *Proc. Natl. Acad. Sci. USA* 87:8331–8335 (1990).

Kornfeld et al., "Assembly of Asparagine–linked Oligosaccharides" *Ann. Rev. Biochem.* 54:631–664 (1985).

Krasney and Young, "Further aspects of IL–1β secretion revealed by transfected monkey kidney cells" *Cytokine* 4(2):134–143 (Mar. 1992).

Kurschner et al., "Construction, purification, and characterization of new interferon γ (IFN γ) inhibitor proteins. Three IFN γ receptor–immunoglobulin hybrid molecules" *Journal of Biological Chemistry* 267(13):9354–9360 (May 5, 1992).

Lasky et al., "Neutralization of the AIDS Retrovirus by Antibodies to a Recombinant Envelope Glycoprotein" *Science* 233:209–212 (1986).

Lesslauer, "Recombinant Soluble Tumor Necrosis Factor Receptor Proteins Protect Mice From Lipopolysaccharide–induced lethality" *European Journal of Immunology* 21:2883–2886 (1991).

Li et al., "Effects of inefficient cleavage of the signal sequence of HIV–1 gp120 on its association with calnexin, folding, and intracellular transport" *Proc. Natl. Acad. Sci. USA* 93(18):9606–9611 (Sep. 3, 1996).

Linsley et al., "Binding of the B Cell Activation Antigen B7 to CD28 Costimulates T Cell Proliferation and Interleukin 2 mRNA Accumulation" *Journal of Experimental Medicine* 173:721–730 (1991).

Linsley et al., "CTLA–4 is a second receptor for the B cell activation antigen B7" *Journal of Experimental Medicine* 174:561–569 (1991).

Machamer and Rose, "Vesicular Stomatitis Virus G Proteins with Altered Glycosylation Sites Display Temperature–Sensitive Intracellular Transport and Are Subject to Aberrant Intermolecular Disulfide Bonding" *Journal of Biological Chemistry* 263(12):5955–5960 (1988).

Mohler et al., "Soluble tumor necrosis factor (TNF) receptors are effective therapeutic agents in lethal endotoxemia and function simultaneously as both TNF carriers and TNF antagonists" *Journal of Immunology* 151(3):1548–1561 (Aug. 1, 1993).

Olden et al., "Role of carbohydrates in protein secretion and turnover: effects of tunicamycin on the major cell surface glycoprotein of chick embryo fibroblasts" *Cell* 13(3):461–473 (Mar. 1978).

Ong and Kern, "The role of glucose and glycosylation in the regulation of lipoprotein lipase synthesis and secretion in rat adipocytes" *Journal of Biological Chemistry* 264(6):3177–3182 (Feb. 25, 1989).

Peppel et al., "A Tumor Necrosis Factor (TNF) Receptor–IgG Heavy Chain Chimeric Protein as a Bivalent Antagonist of TNF Activity" *Journal of Experimental Medicine* 174:1483–1489 (1991).

Rademacher et al., "Glycobiology" *Ann. Rev. Biochem.* 57:785–836 (1988).

Rhodes et al., "Expression, characterization and purification of simian immunodeficiency virus soluble, oligomerized gp160 from mammalian cells" *Journal of General Virology* 75(Pt 1):207–213 (Jan. 1994).

Rickles et al., "Molecular Cloning of Complementary DNA to Mouse Tissue Plasminogen activator mRNA and Its Expression During F9 Teratocarcinoma Cell Differentiation" *Journal of Biological Chemistry* 263(3):1563–1569 (1988).

Ridgway et al., "Expression and Activity of IgE Receptor Alpha Chain–IgG Chimeric Molecules" *Journal of Cell Biology* 115:250a (Abstract No. 1448) (1991).

Stamenkovic et al., "The B Lymphocyte Adhesion Molecule CD22 Interacts with Leukocyte Common Antigen CD45RO on T Cells and α2–6 Sialyltransferase, CD75, on B Cells" *Cell* 66:1133–1144 (Sep. 20, 1991).

Stockert, R., "The asialoglycoprotein receptor: relationships between structure, function, and expression" *Physiological Reviews* 75(3):591–609 (Jul. 1995).

Traunecker et al., "Highly Efficient Neutralization of HIV with Recombinant CD4–immunoglobulin Molecules" *Nature* 339:68–70 (1989).

Watson et al., "A Homing Receptor–IgG Chimera as a Probe for Adhesive Ligands of Lymph Node High Endothelial Venules" *Journal of Cell Biology* 110:2221–2229 (1990).

Watson et al., "Neutrophil Influx into an Inflammatory Site Inhibited by a Soluble Homing Receptor–IgG Chimaera" *Nature* 349:164–167 (1991).

Zhang, et al., Distinct Patterns of Folding and Interactions with Calnexin and Calreticulin in Human Class I MHC Proteins with Altered N–Glycosylation, The Journal of Immunology, vol. 160: 831–837 (1998).

Leung, et al., Engineering a Unique Glycosylation Site for Site–Specific Conjugation of Haptens to Antibody Fragments, The Journal of Immunology, vol. 154: 5919–5926 (1995).

Melcher, et al., Increased Elongation Of N–Acetyllactosamine Repeats In Doubly Glycosylated Lysomzyne With A Particular Spacing Of The Glycosylation Sites, Glycoconjugate Journal, vol. 15: 987–993 (1998).

Brandli, A.W., "Mammalian glycosylation mutants as tools for the analysis and reconstitution of protein transport" *Biochemical Journal* 276:1–12 (1991).

Brousseau et al., "Influence of Tissue Plasminogen Activator (tPA) Propeptide on Recombinant TNFr–IgG1 Expression" *Abstracts of Papers American Chemical Society* (abstract No. 055, presented at the 217th ACS:National Meeting held in Anaheim, CA on Mar. 21–25, 1999) 217(1–2):BIOT 055 (1999).

Haak–Frendscho et al., "Inhibition of TNF by a TNF Receptor Immunoadhesin. Comparison to an Anti–TNF Monoclonal Antibody" *Journal of Immunology* 152:1347–1353 (1994).

Kitaguchi et al., "Enzyme specificity of proteinase inhibitor region in amyloid precursor protein of Alzheimer's disease: different properties compared with protease nexin I" *Biochimica et Biophysica Acta.* 1038(1):105–113 (1990).

Nelles et al., "Characterization of a Fusion Protein Consisting of Amino Acids 1 to 263 of Tissue–type Plasminogen Activator and Amino Acids 144 to 411 of Urokinase–type Plasminogen Activator" *Journal of Biological Chemistry* 262(22):10855–10862 (Aug. 5, 1987).

Sato et al., "The conformation of mature human α–amylase conditions its secretion from yeast" *Gene* 83:355–365 (1989).

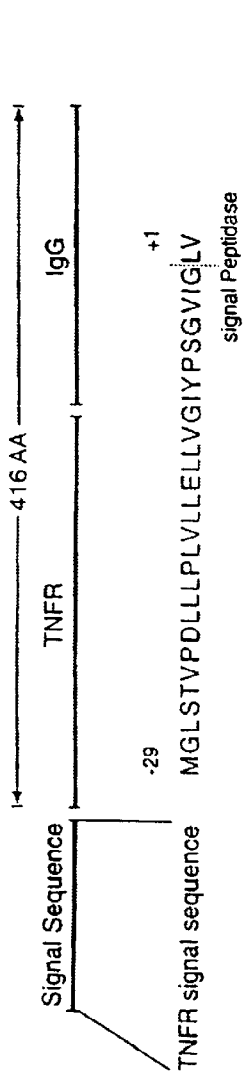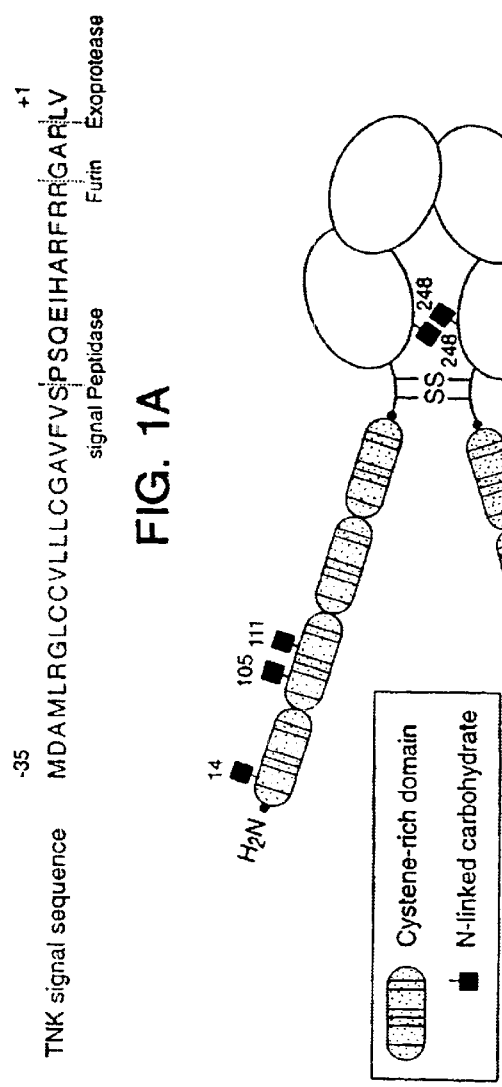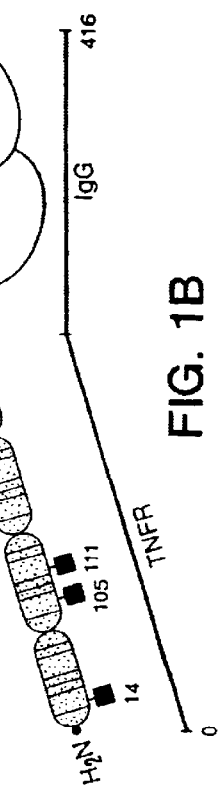
FIG. 1A
FIG. 1B

PROTEIN SECRETION

This application claims benefit of Prov. No. 60/082,002 filed Apr. 16, 1998 and claims benefit of Ser. No. 60/123,522 filed Mar. 8, 1999.

BACKGROUND OF THE INVENTION

1. Field of the Invention

The present invention relates generally to the field of protein production by cell culture. In particular aspects, the invention provides methods and compositions for the production of polypeptides, especially by eukaryotic cell culture, which enhance secretion and facilitate recovery of the polypeptides.

2. Description of Related Disclosures

Many eukaryotic cell surface- and secreted proteins are post-translationally processed to incorporate N-linked and O-linked carbohydrate (Kornfeld and Kornfeld (1985) Annu. Rev. Biochem. 54:631–64; Rademacher et al., (1988) Annu. Rev. Biochem. 57:785–838). Protein glycosylation is thought to subserve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell 81:309–312; Helenius (1994) Mol. Biol. of the Cell 5:253–265; Olden et al., (1978) Cell, 13:461–473; Caton et al., (1982) Cell 37:417–427; Alexander and Elder (1984) Science 226:1328–1330; Flack et al. (1994 J. Biol. Chem. 269:14015–14020). In higher organisms, the nature and extent of glycosylation can markedly affect the circulating half-life and bio-availability of secreted proteins by mechanisms involving receptor mediated uptake and clearance (Ashwell and Morrell (1974) Adv. Enzymol. 41:99–128; Ashwell and Harford (1982) Ann. Rev. Biochem. 51:531–54). Receptor systems have been identified that are thought to play a major role in the clearance of serum proteins through recognition of various carbohydrate structures on the glycoproteins (Stockert (1995) Physiol. Rev. 75:591–609; Kery et al., (1992) Arch. Biochem. Biophys. 298:49–55). Thus, production strategies resulting in incomplete attachment of terminal sialic acid residues might provide a means of shortening the bioavailability and half-life of secreted glycoproteins by promoting clearance by the hepatic asialoglycoprotein receptor. Conversely, expression strategies resulting in saturation of terminal sialic acid attachment sites might lengthen protein bioavailability and half-life by preventing uptake by hepatic receptors. In the development of recombinant glycoproteins for use as pharmaceutical products, it has been speculated that the pharmacodynamics of recombinant proteins can be modulated by the addition or deletion of glycosylation sites from a glycoprotein's primary structure (Berman and Lasky (1985a) Trends in Biotechnol. 3:51–53). However, studies have reported that the deletion of N-linked glycosylation sites often impairs intracellular transport and results in the intracellular accumulation of glycosylation site variants (Machamer and Rose (1988) J. Biol. Chem. 263:5955–5960; Gallagher et al., (1992) J. Virology 66:7136–7145; Collier et al., (1993) Biochemistry 32: 7818–7823; Claffey et al., (1995) Biochemica et Biophysica Acta 1246:1–9; Dube et al., (1988) J. Biol. Chem. 263:17516–17521). While glycosylation site variants of secreted proteins can be expressed intracellularly, it has proved difficult to recover useful quantities from growth conditioned cell culture medium.

It has been shown that impaired secretion of the HIV-1 envelope glycoprotein containing N-linked carbohydrate structures can be partially overcome by replacing the native signal sequence of the glycoprotein with the signal sequence and 5' untranslated region of the herpes simplex virus type 1 glycoprotein D (HSV gD-1) (Lasky et al., (1986) Science 233:209–212; Berman et al., (1989) J. Virol. 63:3489–3498). Studies have reported the use of the native secretory peptide of human tissue type plasminogen activator in cell culture production of non-t-PA glycoproteins (International Publication No. WO 96/17067; Krasney and Young (1992) Cytokine 4:134–143; Rhodes et al., (1994) J. Gen. Virol. 75:207–213). None have reported a strategy for the secretion and recovery of proteins wherein one or more native glycosylation sites have been added to or deleted from the protein's primary structure.

SUMMARY OF THE INVENTION

The present invention provides methods and compositions useful in the production of proteins by recombinant cell culture. The methods and compositions overcome intracellular retention of proteins and facilitate extracellular recovery of the produced proteins. In particular embodiments, the invention provides methods and compositions for the production of polypeptides other than tissue-type plasminogen activators (t-PA's) utilizing a precursor peptide corresponding to the amino terminal signal and/or pro peptides naturally associated with a mammalian t-PA which act to direct the secretion of the mature t-PA. In particular embodiments, the invention provides for the export and secretion of polypeptides other than t-PA's. For example, the invention provides methods and compositions useful in the recombinant production and extracellular recovery of novel chimeric or fusion proteins such as immunoadhesins and especially those with poor secretion kinetics. In particular embodiments the invention provides for the production and recovery of glycoproteins that have been altered from their native sequence to add or remove one or more glycosylation sites. Advantageously, the invention improves and in preferred embodiments restores the export and secretion of such glycosylation site variants. It is a further advantage of the present invention that greater quantities of the polypeptides produced utilizing the compositions and methods of the present invention can be recovered from the extracelluar medium of the cultured cells from which they are produced.

Accordingly, in particular embodiments, the invention provides nucleic acids, expression systems and host cells, as well as methods for the production of non t-PA polypeptides, such as immunoadhesins and especially glycosylation site variant polypeptides, in cell culture. In one embodiment of the present invention, a DNA construct is provided for the export and secretion of such polypeptides comprising a first DNA segment encoding a precursor peptide corresponding to all or a portion of the amino terminal signal and/or pro peptides naturally associated with a mammalian and preferably a human t-PA. The first DNA segment is operably linked, in frame, to a second DNA segment encoding the heterologous (non-t-PA) polypeptide. In particular aspects, the first DNA segment encodes a peptide corresponding to a mammalian and preferably a human t-PA pro-sequence as defined herein. According to this aspect of the present invention, the first DNA segment is operably linked to a second DNA segment encoding a heterologous polypeptide.

Certain embodiments additionally comprise a DNA segment encoding a peptide corresponding to a mammalian signal and or pro-peptide upstream of and operably linked to the first DNA segment. For example, when the heterologous polypeptide is an immunoadhesin, such as a TNFR-IgG chimera, the first DNA segment may be preceded by a DNA segment encoding a mammalian t-PA or, alternatively, a heterologous signal and or pro-sequence. According to this aspect of the invention the mammalian t-PA signal sequence or other heterologous signal and or pro-sequence and the pro-peptide amino acid sequence comprise the precursor peptide of the invention.

In preferred embodiments, the first DNA segment encodes a native or naturally occurring signal and pro peptide of a mammalian t-PA and especially a human t-PA. The second DNA sequence preferably encodes a polypeptide other than a mammalian t-PA such as, for example, an immunoadhesin. According to further aspects of the invention, the second DNA sequence encodes a naturally occurring or chimeric polypeptide other than a mammalian t-PA wherein one or more glycosylation sites have been added to or deleted from the polypeptide's native sequence. The invention further provides a DNA construct comprising one or more additional DNA segments operably linked to the first and second DNA segments.

The invention further provides a cultured eukaryotic host cell comprising a DNA construct having a first DNA segment encoding a precursor peptide the precursor peptide corresponding to all or a portion of a mammalian t-PA signal and or pro peptide and a second DNA segment operably linked to the first DNA sequence, the second DNA sequence encoding a polypeptide other than a mammalian t-PA and preferably a polypeptide other than a mammalian t-PA wherein one or more glycosylation sites have been added to or deleted from the polypeptide.

The invention further provides methods of producing a heterologous polypeptide especially a polypeptide which has been altered to delete one or more native N-linked glycosylation sites comprising the steps of (a) culturing a eukaryotic host cell comprising a DNA construct, the DNA construct comprising:
a first DNA segment encoding a precursor peptide corresponding to all or a portion of a mammalian tissue plasminogen activator signal and or pro peptide; and
a second DNA segment operably linked to the first DNA sequence, the second DNA sequence encoding a polypeptide other than t-PA wherein one or more native N-linked glycosylation sites of the polypeptide have been deleted from the polypeptide wherein the eukaryotic host cell expresses the first and second DNA segments and the polypeptide is secreted from the cell; and (b) recovering the polypeptide so produced.

BRIEF DESCRIPTION OF THE DRAWINGS

FIG. 1. Diagram of a tumor necrosis factor immunoglobulin chimeric molecule (TNFR-IgG1) and signal sequences. TNFR-IgG1 is a chimeric protein consisting of the extracellular domain of the p55 TNF receptor fused to the hinge and Fc domain of an immunoglobulin heavy chain. TNFR-IgG1 is secreted as a homodimer with four N-linked glycosylation sites (squares) per monomer. The proteins expressed in this study were synthesized using the wild type TNFR signal sequence containing 29 amino acids (SEQ ID NO: 2), or a combination of the TNFR signal sequence and the signal and/or pro-sequence of human tissue plasminogen activator (tPA) (SEQ ID NO: 1).

FIG. 2A, intracellular (i.e. cell associated) TNFR-IgG1; FIG. 2B, Secreted TNFR-IgG1; FIG. 2C, intracellular tPA.TNFR.IgG; FIG. 2D, secreted tPA.TNFR.IgG.

FIG. 3A, TNFR-IgG1; FIG. 3B, tPA.TNFR-IgG1; FIG. 3C, TNFR-IgG1 mutant lacking 2 native glycosylation sites (NNQQ); FIG. 3D, tPA.NNQQ; FIG. 3E, QSNQ; FIG. 3F, tPA.QSNQ.

DETAILED DESCRIPTION OF THE PREFERRED EMBODIMENTS

Definitions

Figure 2A:
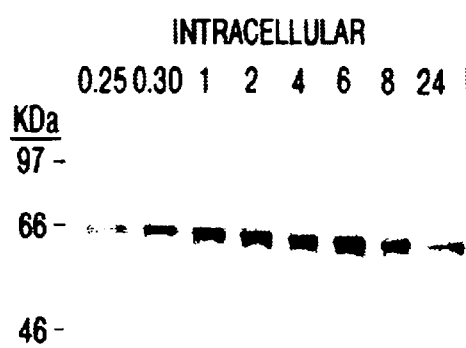
FIGS. 2A–2D. Effect of the signal sequence on the secretion kinetics of TNFR-IgG1 and tPA.TNFR-IgG1. Parallel cultures of human embryonic kidney cells were transfected with plasmids encoding either TNFR-IgG1 utilizing the native signal sequence or the signal and pro-sequence of t-PA (tPA.TNFR-IgG1) for pulse labeling experiments. Two days post-transfection the culture, medium was removed and replaced (after washing two times) with methionine- and cysteine-free DMEM supplemented with ($^{35}$S)-labeled methionine and cysteine. Cells were labeled at 37° C. (5% $CO_2$) for the times indicated. The labeling reaction was terminated by washing the cells immediately in chilled (4° C.) PBS followed by detergent extraction. Cell lysates and cell culture supernatants were precipitated by the addition of Protein A SEPHAROSE™. The Protein A:TNFR-IgG1 complexes were pelleted by centrifugation, washed repeatedly and eluted in SDS-PAGE sample buffer containing mercaptoethanol. The eluted protein was resolved on 10% SDS-PAGE gels and visualized by autoradiography.
Figure 2B:
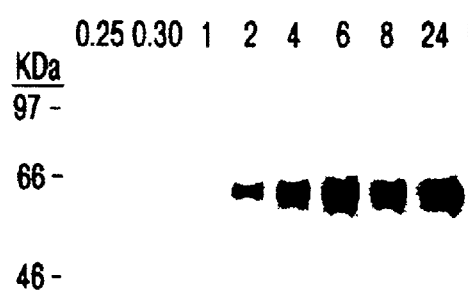
Figure 2C:
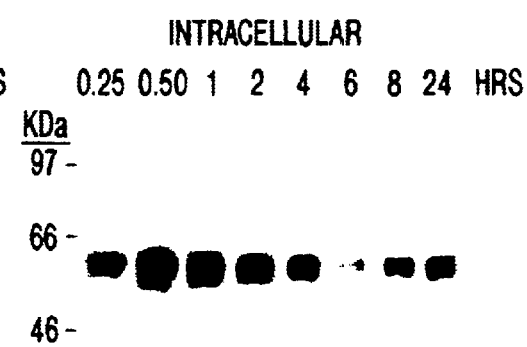
Figure 2D:
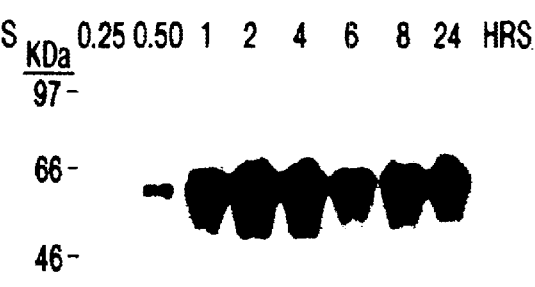

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for a particular amino acid sequence of a polypeptide.

The terms "t-PA" and "tissue plasminogen activator" refer to a naturally occurring extrinsic (tissue-type) plasminogen activator having fibrinolytic activity and typically having a structure with five domains (finger, growth factor, kringle-1, kringle-2, and protease domains). Naturally occurring mammalian t-PA includes human species as well as other animal species such as rabbit, rat, porcine, non human primate, equine, murine, and ovine t-PA. Nucleic acids encoding t-PA from human and non-human species is known in the art. For example, human t-PA is encoded by the cDNA sequence reported in U.S. Pat. No. 4,766,075, issued Aug. 23, 1988.

A "precursor peptide" as used in the context of the present invention and as more fully described herein below, is used to refer to a polypeptide having an amino acid sequence corresponding to all or a portion of a naturally occurring mammalian t-PA signal and/or pro peptide which participates in the secretion of t-PA under native conditions.

"Pre-pro" or "signal-pro" peptide as used in the context of the present invention is meant to refer to an amino acid sequence such as that naturally associated with a mammalian t-PA which acts to direct the secretion of a mature polypeptide, for example, a mammalian t-PA, from a cell. As used herein, the term "signal-pro peptide" includes the "pre-" or "signal" sequence such as that naturally associated with a mammalian t-PA which functions to bind to the signal-recognition particle and direct the protein to the lumen of the endoplasmic reticulum (ER). A "signal" sequence is an amino acid sequence, characteristically hydrophobic in nature, cleaved by signal peptidases in the ER. For example, the signal sequence of t-PA is generally removed from the nascent t-PA co-translationally. In addition to a signal sequence, some mammalian proteins are associated post-translationally with a "pro" sequence such as the signal-pro sequence of a mammalian t-PA. The "pro-" sequence serves to target the nacsent polypeptide, for example a mature t-PA, to the Golgi apparatus (GA) and is cleaved post-translationally. The pro-sequence is characteristically positively charged and commonly contains golgi peptidase cleavage sequences.

The amino acid sequences of the mammalian t-PA signal-pro peptides are generally known or obtainable through conventional techniques. Signal-pro peptides from human and non-human t-PAs are known in the art and have been disclosed in, for example U.S. Pat. No. 4,766,075; Rickles et al., (1988) J. Biol. Chem. 263:1563–1560 and Feng et al., (1990) J. Biol. Chem. 265:2022–2027. The term native signal-pro peptide specifically encompasses naturally-occurring pre- and prepro-sequences as defined and includes naturally-occurring variant forms (e.g., alternatively spliced forms) and naturally-occurring allelic variants of the t-PA signal-pro peptide. DNA sequences encoding mammalian t-PA amino terminal signal-pro peptides can be cloned as cDNA or genomic molecules according to techniques that are standard in the art or can be synthesized, preferably using automated equipment and the application of conventional synthetic protocols.

As used herein, "heterologous polypeptide" refers generally to polypeptides and proteins regardless of their origin other than a t-PA or a variant thereof and generally having more than about ten amino acids which may or may not have one or more native or synthetic sites for the attachment of a carbohydrate. Preferably, heterologous polypeptides are "heterologous glycoproteins", that is a heterologous polypeptide as described above having one or more sites for the attachment of a carbohydrate in their native sequence. Examples of heterologous glycoproteins include molecules such as cytokines and their receptors, as well as chimeric proteins comprising cytokines or their receptors, including, for instance tumor necrosis factor alpha and beta, their receptors (TNFR-1; Gray et al., (1990) Proc. Natl. Acad. Sci. USA 87:7380–7384; and TNFR-2; Kohno et al., (1990) Proc. Natl. Acad. Sci. USA 87:8331–8335) and their derivatives; renin; a growth hormone, including human growth hormone, and bovine growth hormone; growth hormone releasing factor; parathyroid hormone; thyroid stimulating hormone; lipoproteins; alpha-1-antitrypsin; insulin A-chain; insulin B-chain; pro insulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp 120, gp 160 or fragments thereof; transport proteins; homing receptors; addressins; regulatory proteins; antibodies and chimeric proteins, such as immunoadhesins.

Preferably the heterologous glycoproteins are "glycosylation site variants" of any of the heterologous glycoproteins described above. More particularly, the glycosylation site variants according to the present invention are naturally occurring heterologous glycoproteins or variations thereof such as the chimeric proteins described above, having at least one site for glycosylation, preferably an N-linked glycosylation site, that has been added to or deleted from their native sequence. Such glycosylation site variants include both "glycosylation site addition variants" as well as "glycosylation site deletion variants" so named herein to delineate heterologous glycoproteins as defined above having one or more sites for glycosylation, preferably N-linked, added to or deleted from their native sequence, respectively.

The heterologous glycoproteins of the present invention have one or more carbohydrate structures that occur on the native protein expressed as N-linked or O-linked carbohydrates. The N-linked and O-linked carbohydrates differ primarily in their core structures. N-linked glycosylation refers to the attachment of the carbohydrate moiety via N-acetylglucosamine (GlcNAc) to an asparagine residue in the peptide chain. The amino acid sequence of the heterologous polypeptide will contain an asparagine-X-serine, asparagine-X-threonine, or asparagine-X-cysteine, wherein X is any amino acid except proline. O-linked carbohydrates, by contrast are characterized by a common core structure, which is the N-acetylgalactosamine (GalNAc) attached to the hydroxyl group of a threonine or serine in the native amino acid sequence of the heterologous polypeptide.

The terms "tumor necrosis factor receptor" and "TNFR" in the context of the present invention refer to a polypeptide comprising the amino acid sequence of a native TNF binding polypeptide, or any combination, derivative or fragment thereof which is capable of binding to tumor necrosis factor-α and/or -β (TNF-α and/or -β). This definition includes substantially intact cell surface or soluble type 1 and type 2 TNFR polypeptides (TNFR1 and TNFR2) from natural sources, synthetically produced in vitro or obtained by genetic manipulation including methods of recombinant DNA technology, as well as various chain combinations of such polypeptides. Native TNFR include human and non-human animal, e.g. murine, bovine, equine, porcine, etc. TNFR polypeptides. The non-human mammalian species can, for example, be obtained by cross-species hybridization, using probes obtained from the human DNA sequence as hybridization probes to isolate TNFR cDNAs from the respective non-human mammalian cDNA libraries.

The chimeric gene encoding TNFR1-IgG1 is described in Ashkenazi et al., (1991) Proc. Natl. Acad. Sci. 88:10535–10539. TNFR1-IgG1 is a chimeric protein constructed by fusing the extracellular domain of the receptor type 1 for TNF alpha with sequences encoding the Fc domain and hinge region of IgG1 (Ashkenazi et al., (1991). The chimeric protein (FIG. 1) contains four N-linked glycosylation sites: three located in the TNFR region (positions 14, 105, and 111) and one in the Fc domain (position 248). For simplicity, the glycosylation mutants described in this invention are named using the single letter amino acid code with reference to the amino acid residue present at each of the four N-linked glycosylation sites at amino acid positions 14, 105, 111, and 248 (FIG. 1). Thus, the designation NNNN represents the fully glycosylated TNFR1-IgG1, whereas NQNN indicates TNFR-IgG1 where glutamine replaced asparagine at the second glycosylation site (position 105).

As used herein, the term "immunoadhesin" designates antibody-like molecules which combine the "binding domain" of a heterologous protein (an "adhesin", e.g. a receptor, ligand or enzyme) with the effector functions of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as $IgG_1$, $IgG_2$, $IgG_3$, or $IgG_4$ subtypes, IgA, IgE, IgD or IgM. Immunoadhesins are described in, for example, U.S. Pat. Nos. 5,116,964, 5,714,147 and 5,336,603 the disclosures of which are hereby incorporated by reference. Immunoadhesins include CD4 (Capon et al., (1989) Nature 337:525–531; Traunecker et al., (1989) Nature 339:68–70; and Byrn et al., (1990) Nature 344:667–670); L-selectin or homing receptor (Watson et al., (1990) J. Cell. Biol. 110:2221–2229; and Watson et al., (1991) Nature 349:164–167); CD44 (Aruffo et al., (1990) Cell 61:1303–1313; CD28 and B7 (Linsley et al., (1991) J. Exp. Med. 173:721–730); CTLA-4 (Lisley et al., J. Exp. Med. 174:561–569); CD22 (Stamenkovic et al., Cell 66:1133–1144); TNF receptor (Ashkenazi et al., (1991) Proc. Natl. Acad. Sci. USA 88:10535–10539; Lesslauer et al., (1991) Eur. J. Immunol. 27:2883–2886; and Peppel et al., (1991) J. Exp. Med. 174:1483–1489; Mohler et al., (1993) J. Immunol. 151:1548–1561); NP receptors (Bennett et al., (1991) J. Biol. Chem. 266:23060–23067; interferon γ receptor (Kurschner et al., (1992) J. Biol. Chem. 267:9354–9360; 4-1BB (Chalupny et al., (1992) PNAS USA 89:10360–10364) and IgE receptor α (Ridgway and Gorman, (1991) J. Cell. Biol. 115, Abstract No. 1448).

The terms "host cell" and "host cell line" refer to cells and cell lines derived from a prokaryotic or eukaryotic organism that are capable of growth and survival when placed in either monolayer culture or in suspension culture in a medium containing the appropriate nutrients and growth factors. Suitable host cells for use within the present invention include any type of cell that can be engineered to express a DNA molecule, can be grown in culture, and have a secretory pathway. Although prokaryotic cells such as E. coli cells are capable of secreting protein at least into the periplasmic space, it is preferred within the context of the present invention to use cultured eukaryotic cells, such as fungal cells, insect cells, yeast cells or in particular mammalian cells. The necessary growth factors for a particular cell line are readily determined empirically without undue experimentation, as described for example in *Mammalian Cell Culture* (Mather, J. P. ed., Plenum Press, N.Y. [1984]), and Barnes and Sato, (1980) Cell, 22:649. Typically, the cells are capable of expressing and secreting large quantities of a particular glycoprotein of interest into the culture medium. Examples of such cells include SF9 insect cells (Summers and Smith (1987) Texas Agriculture Experiment Station Bulletin, 1555; and Insect Cell Culture Engineering, Goosen Daugulis and Faulkner Eds. Dekker, New York). Examples of suitable mammalian host cells within the context of the present invention may include Chinese hamster ovary cells/-DHFR (CHO, Urlaub and Chasin, Proc. Natl. Acad. Sci. USA, 77:4216 [1980]); dp12.CHO cells (EP 307,247 published Mar. 15, 1989); monkey kidney CV1 line transformed by SV40 (COS-7, ATCC CRL 1651); human embryonic kidney line (293 or 293 cells subcloned for growth in suspension culture, Graham et al., J. Gen Virol., 36:59 [1977]); baby hamster kidney cells (BHK, ATCC CCL 10); mouse sertoli cells (TM4, Mather, Biol. Reprod., 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44–68 [1982]); MRC 5 cells; FS4 cells; and a human hepatoma line (Hep G2).

Preferred host cells include Chinese hamster ovary cells/-DHFR (CHO, Urlaub and Chasin, Proc. Natl. Acad. Sci. USA, 77:4216 [1980]); dp12.CHO cells (EP 307,247 published Mar. 15, 1989).

"Expression vector" refers to a DNA construct containing a DNA sequence which is operably linked to a suitable control sequence capable of effecting the expression of the DNA in a suitable host. Such control sequences include a promoter to effect transcription, an optional operator sequence to control such transcription, optional RNA splice donor/acceptor sequences, a sequence encoding suitable mRNA ribosome binding sites, and sequences which control termination of transcription and translation. The vector may be a plasmid, a phage particle, a recombinant virus or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"Operably linked" when describing the relationship between two DNA regions simply means that they are functionally related to each other. For example, a signal sequence is operably linked to a peptide if it functions to ensure synthesis on membrane bound ribosomes and to translocate the nascent protein across the lumen of the endoplasmic reticulum as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation. Therefore, nucleic acid is "operably linked" when it is placed into a functional relationship with another nucleic acid sequence. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "transfected," "transformed (host) cell" , "transfectant" and "transformed" and the like refer to the introduction of DNA into a cell. The cell is termed a "host cell". The introduced DNA is usually in the form of a plasmid derived vector containing an inserted piece of DNA. The introduced DNA sequence may be from the same species as the host cell or a different species from the host cell, or it may be a hybrid DNA sequence, containing some foreign and some homologous DNA. The words transformants and transformed (host) cells include the primary subject cell and cultures derived therefrom, without regard to the number of transfers. It is also understood that all progeny may not be precisely identical in DNA content, due to deliberate or inadvertent mutations or amplification of chromosomal fragments. Mutant progeny that have the same function or biological property as screened for in the originally transformed cell are included. The term amino acid or amino acid residue, as used herein, refers to naturally occurring L amino acids or residues, unless otherwise specifically indicated. The commonly used one- and three-letter abbreviations for amino acids are use herein (Lehninger, A. L., *Biochemistry*, 2d ed., pp. 71–92, Worth Publishers, N.Y. (1975)).

Modes for Carrying Out the Invention

Studies have demonstrated that deletion of N-linked glycosylation sites from a glycoprotein's primary structure often impairs the intracellular transport and secretion of the polypeptide. According to the present invention, the defect in secretion of such polypeptides can be overcome by operably linking the nucleic acid sequence encoding the polypeptide to a nucleic acid sequence encoding a precursor peptide. Surprisingly, the precursor polypeptide increased the secretion efficiency of the parent glycoprotein as well. The precursor peptide has an amino acid sequence which correspond to all or a portion of a naturally occurring mammalian t-PA signal-pro peptide which participates in the secretion of t-PA under native conditions.

Preferably the precursor peptide of the present invention is "capable of restoring the export and secretion" of a heterologous polypeptide, especially a heterologous glycoprotein such as an immunoadhesin and more preferably a heterologous glycosylation site variant glycoprotein to the extracellular space. As will be appreciated by the skilled artisan "capable of restoring the export and secretion" of a polypeptide to the extracellular space is a relative term. Thus the term when used to describe the biological activity of the precursor peptide means a peptide that when linked to a heterologous polypeptide produces an increase in the amount of heterologous polypeptide that can be recovered from the extracellular space when compared to the amount recoverable from the extracellular space in the absence of the precursor peptide of the present invention and in the presence of the native signal and/or pro sequence of the heterologous polypeptide.

To determine whether the precursor peptide improves the export and secretion of the polypeptide, the efficiency of intracellular transport can be measured by routine experimentation. For example, a plasmid can be constructed for transient transfection studies in eukaryotic host cells. Pulse-chase experiments similar to those described herein will show that replacement of the native signal sequence associated with the heterologous polypeptide with the precursor peptide of the present invention results in an improvement in secretion efficiency. Thus, after transient expression at, for example 24 hours, the amount of heterologous polypeptide secreted into the culture medium can be measured and compared to a control using a native or other signal sequence. For example, approximately 70–80% and preferably 80–100% of the pulse-labeled heterologous polypeptide can be secreted into the cell culture medium when a precursor peptide of the present invention is employed in the expression construct, whereas only 50–60% of the heterologous polypeptide is secreted using the wild-type or native signal sequence. This represents a 20 to 50% increase in secretion efficiency.

The increased efficiency of secretion achieved according to the present invention utilizing the precursor peptide is also apparent from the kinetics of secretion of the heterologous polypeptide. For example, when the native signal sequence is employed, 40% of the pulse-labeled heterologous polypeptide is secreted in 2–4 hrs. after pulse labeling. However when the native signal sequence is replaced with the precursor peptide corresponding to a mammalian t-PA signal-pro peptide, approximately 60% of the heterologous polypeptide is secreted in this time frame.

The precursor peptide of the present invention has an amino acid sequence which corresponds to all or a portion of the amino acid sequence of a mammalian t-PA signal-pro peptide including native signal-pro peptides of t-PA having the same amino acid sequence as a signal-pro peptide of a mammalian t-PA sequence derived from nature. Using human t-PA as but an example, the signal-pro peptide precedes the mature t-PA protein sequence and acts to direct export and secretion of the mature protein. The approximately 35 amino acid signal pro-peptide of human t-PA consists of a signal sequence of about 21 (SEQ ID NO: 3) or 22 (SEQ ID NO: 12) amino acid residues, also called a pre-sequence, and an 11 (SEQ ID NO: 4) or 10 (SEQ ID NO: 13) amino acid pro-sequence, including a 3 amino acid exopeptidase cleavage site (see, for example, FIG. 1 infra; Example 8, infra; and Berg and Grinnell (1991) Biochem. Biophys. Res. Commun. 179:31289–1296). However, it is the ability of the precursor peptide to restore or increase export and secretion of the heterologous polypeptide and not the length of the precursor peptide that is important. Therefore, in one embodiment of the invention, the signal-pro peptide of a mammalian t-PA is a native human sequence comprising amino acids 1 to 35 of SEQ ID NO: 1 numbered as shown below and corresponding to amino acids −35 to −1 of FIG. 1. Therefore, in general the present invention makes use of a precursor peptide having the sequence:

1 2 3 4 5 6 7 8 9 10 11 12 13 14 15 16 Met-Asp-Ala-Met-Lys-Arg-Gly-Leu-Cys-Cys-Val-Leu-Leu-Leu-Cys-Gly-17 18 19 20 21 22 23 24 25 26 27 28 29 30 31 32 Ala-Val-Phe-Val-Ser-Pro-Ser-Gln-Glu-Ile-His-Ala-Arg-Phe-Arg-Arg-33 34 35 Gly-Ala-Arg (SEQ ID NO: 1).

In another embodiment of the invention, the precursor peptide comprises a human t-PA pro-sequence as, for example, amino acids 22 to 32 (SEQ ID NO: 4) of SEQ ID NO: 1, or amino acids 22–35 (SEQ ID NO: 5) of SEQ ID NO: 1 and more preferably amino acid residues 23–35 of SEQ ID NO: 1 (SEQ ID NO: 7). In another embodiment of the invention, the precursor peptide is a human signal-pro sequence comprising amino acids 1 to 32 (SEQ ID NO: 6) of SEQ ID NO: 1 and preferably amino acid residues 1–35 (SEQ ID NO: 1). Such precursor peptides and the DNA encoding them can be isolated from nature or can be produced by recombinant or synthetic means.

In a further aspect of the present invention the precursor peptides of the present invention are homologous amino acid sequences of mammalian t-PA's signal-pro peptides or homologous amino acid sequences of the sequence of, for example, SEQ ID NO: 1, SEQ ID NO: 3, SEQ ID NO: 4, SEQ ID NO: 5, SEQ ID NO: 6, and SEQ ID NO: 7 including homologous in vitro generated variants having the qualitative biological activity defined above. Homology with respect to the precursor peptides of the present invention is defined as the percentage of amino acid residues in a candidate sequence that are identical with either the amino acid residues in SEQ ID NO: 1, SEQ ID NO:3, SEQ ID NO:4, SEQ ID NO:5, SEQ ID NO: 6, SEQ ID NO: 7, the amino acid sequence of a mammalian t-PA or a composite sequence of a human and other mammalian sequence as defined herein after aligning the sequences and introducing gaps if necessary to achieve the maximum identity. No N- or C- terminal extensions or deletions in the candidate sequence shall be construed as reducing identity. For example, N- or C-terminal addition of a signal sequence other than that of a mammalian t-PA to mammalian precursor peptide as defined herein is within the scope of the precursor peptide of the invention. "Composite amino acid" within the present invention refers to an alternate amino acid having the same position in the 35 amino acid residue structure as human t-PA from another mammalian vertebrate species. Therefore, an amino acid substitution referred to as a composite amino acid substitution replaces the identified amino acid with the equivalent or composite amino acid from another mammalian species. A composite sequence is defined as having at least one amino acid from the native human t-PA sequence replaced with a composite amino acid from another mammalian species.

Therefore, the invention contemplates an precursor peptide having at least the qualitative biological activity as defined above and having, for example, at least about 75% amino acid homology with the polypeptide of SEQ ID NO: 1, SEQ ID NO: 3, SEQ ID NO: 4 or the polypeptide of SEQ ID NO: 1 lacking the 3 carboxyl terminal amino acid residues, SEQ ID NO: 6 and/or the 21 amino terminal residues, SEQ ID NO: 5. The precursor peptide amino acid sequence preferably will share at least 80%, more preferably, greater than 85% sequence homology with the sequence of SEQ ID NO: 1 or the sequences lacking the 3 carboxyl terminal amino acid residues (SEQ ID NO: 6) and/or the 21 amino terminal residues (SEQ ID NO: 5).

However, a precursor peptide may exhibit less than 50% sequence homology with the sequence of SEQ ID NO: 1 and still retain the characteristics of the precursor peptide as defined above.

Since the mechanism by which the signal-pro peptide of t-PA overcomes endoplasmic reticulum retention may relate to its complex structure, precursor peptides which comprise a portion of a signal-pro peptide as defined above are also within the scope of the present invention. For example, as noted above, the signal-pro peptide of t-PA is unusual, and contains an approximately 21–22 amino acid pre- or signal sequence and a 10 or 11 amino acid pro-sequence, including a 3 amino acid exopeptidase cleavage site (FIG. 1). Previous studies, (Berg and Grinnell (1991) Biochem. Biophys. Res. Commun. 179:1289–1296) have shown that the pre- or signal sequence is cleaved co-translationally in the endoplasmic reticulum and that the pro-sequence is removed in the Golgi apparatus (GA) by cleavage at a furin processing site. The fact that the endo H sensitive, intracellular forms of an exemplary heterologous glycoprotein glycosylation site variant expressed with the amino terminal precursor peptide sequence of the present invention possessed higher molecular weight than the secreted products demonstrates that, like wild type t-PA, removal of the pro-sequence from glycosylation mutants occurs during export through the GA. Based on these observations, the amino terminal pro-sequence of t-PA represents a structural element able to promote ER to GA transport of the heterologous polypeptide, and especially glycosylation mutants.

Therefore according to a preferred aspect of the present invention, a precursor peptide comprising all or a portion of the pro-sequence of a mammalian-tPA is employed to effect the export and secretion of the heterologous polypeptides of the present invention. For example, the pre-sequence of any mammalian pre-protein sequence, for example, that associated with the native heterologous polypeptide, may be employed in conjunction with the pro-sequence of a mammalian t-PA in the precursor peptide of the present invention. For example, insertion of the 13 amino acid tPA pro-peptide Ser-Gln-Glu-Ile-His-Ala-Arg-Phe-Arg-Arg-Gly-Ala-Arg (SEQ ID NO: 7) between the TNFR1-IgG1 endogenous signal sequence, i.e., that naturally associated with TNFR1 (Gray et al., (1990) supra, amino acids −40 to −12 of FIG. 1, SEQ ID NO: 2) and the TNFR1-IgG1 coding sequence provides a precursor peptide (SEQ ID NO: 8) within the context of the present invention that exhibits an increase in export and secretion of the mature molecule (TNFR1-IgG1).

According to another aspect of the present invention the DNA sequence of the t-PA pro-sequence (SEQ ID NO: 5; SEQ ID NO: 7) is modified to introduce or eliminate proteolytic processing sites. Such modified precursor peptides are described in, for example, International publication No. WO 96/17067. Briefly, and while not wishing to be bound by theory it is believed that pro-sequence of mammalian t-PA is cleaved at a site dependent upon a prohormone converting enzyme such as the yeast KEX2 gene product or the mammalian enzymes PC1, PC2 and furin. Enzymes of this type recognize cleavage sites characterized by arginine residues in the −1 and −4 positions. Cleavage is facilitated by a basic amino acid residue e.g. Lys or Arg in the −1 position. Within the present invention therefore are a pro-sequence having an Arg at residue 35 and 32 and optionally a basic amino acid residue at position 34.

As indicated, the present invention further comprises a second DNA segment encoding a heterologous polypeptide, i.e., a polypeptide other than a mammalian t-PA such as a TNFR immunoadhesin. Preferably the heterologous polypeptide lacks or has been modified to delete one or more native glycosylation sites as described.

Deletion of glycosylation sites from a heterologous polypeptide may be accomplished by altering the amino acid sequence of the polypeptide. The alteration may be made by, for example, the addition of or substitution by one or more amino acids to the polypeptide's native sequence. For example, if N-linked glycosylation is contemplated, the glycosylation site in the variant is a tripeptidyl sequence of the formula: asparagine-X-serine or asparagine-X-threonine, wherein asparagine is the acceptor and X is any of the twenty genetically encoded amino acids except proline. (See Struck, D. K. and Lennarz, W. J. in *The Biochemistry of Glycoproteins and Proteoglycans*, W. J. Lennarz ed., Plenum Press, 1980, p. 35; Marshall, R. D. (1974) Biochem. Soc. Symp. 40:17; and Winzler, R. J. in *Hormonal Proteins and Peptides*, Li, C. I. ed., Academic Press, New York, 1973, pp. 1–15). The amino acid sequence variants herein are modified by substituting the appropriate amino acid(s) at the proper site(s) to effect a change in the native glycosylation site. For example an asparagine residue can be replaced by a glutamine residue to disrupt a native glycosylation site within the polypeptide.

If O-linked glycosylation is to be employed, O-glycosidic linkage occurs in animal cells between N-acetylgalactosamine, galactose or xylose, and one of several hydroxyamino acids, most commonly serine or threonine, but also in some cases a 5-hydroxyproline or 5-hydroxylysine residue placed in the appropriate region of the molecule.

According to the present invention the polypeptides are altered through changes at the DNA level, particularly by mutating the DNA encoding the polypeptide at preselected bases, i.e., those encoding N- or O-linked glycosylation sites such that codons are generated that will translate into amino acids other than those that will typically be present for N- or O-linked glycosylation. The variations can be made using methods known in the art such as oligonucleotide-mediated (site directed) mutagenesis, alanine scanning and PCR mutagenesis. Site directed mutagenesis (Carter et al., (1986) Nucl. Acids Res. 13:4331; Soller et al., (1987) Nucl. Acd. Res., 10:6487, cassette mutagenesis (Wells et al., (1985) Gene 34:315), restriction selection mutagenesis (Wells et al., (1986) Philos. Trans. R. Soc. London) or other known techniques can be performed on the cloned DNA to produce the glycosylation site mutants that are a subject of the present invention.

Therefore, according to the present invention in order to direct the secretion of a heterologous polypeptide and preferably a glycosylation variant as described above, a DNA segment encoding a precursor peptide is joined to a DNA sequence encoding the heterologous polypeptide in the correct reading frame so that the joined sequences encode a fusion protein.

Expression vectors for use in the methods and compositions of the present invention will generally include a promotor capable of directing the transcription of the first and second DNA of the invention. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. Preferred promoters include viral promoters and cellular promoters.

Host cells are transfected or transformed with expression or cloning vectors described herein for heterologous polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation, as well as the use of commercially available cationic lipid reagents which facilitate transfection. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Soling en et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 185:527–537 (1990) and Mansour et al., *Nature*, 336:348–352 (1988).

Suitable host cells for the expression of heterologous polypeptide that retain one or more glycosylation sites are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Host cells containing DNA constructs of the present invention are then cultured to produce the heterologous protein. The cells ate cultured according to standard methods in a culture medium containing the necessary nutrients for growth of cultured mammalian cells.

For the culture of the eukaryotic cells expressing the desired protein and modified as described for the instant invention, numerous culture conditions can be used paying particular attention to the host cell being cultured. Suitable culture conditions for eukaryotic cells are well known in the art (J. Immunol. Methods (1983)56:221–234) or can be easily determined by the skilled artisan (see, for example, *Animal Cell Culture: A Practical Approach* 2nd Ed., Rickwood, D. and Hames, B. D., eds. Oxford University Press, New York (1992)), and vary according to the particular host cell selected.

The eukaryotic cell culture of the present invention is prepared in a medium suitable for the particular cell being cultured. Commercially available media such as Ham's F10(Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace,(1979) Meth. Enz., 58:44; Barnes and Sato,(1980) Anal. Biochem., 102:255; U.S. Pat. Nos. 4,767,704; 4,657,866; 4,927,762; 5,122,469 or 4,560,655; International Publication Nos. WO 90/03430; and WO 87/00195; the disclosures of all of which are incorporated herein by reference, may be used as culture media. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art.

In a particular embodiment, the mammalian host cell is a CHO cell, preferably a DHFR-CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346–349) (the formulation of medium as described in U.S. Pat. No. 5,122,469 are particularly appropriate) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; Gentamycin; and trace elements.

For the production of the sought after glycoproteins, production by growing the host cells of the present invention under a variety of cell culture conditions is typical. For instance, cell culture procedures for the large or small scale production of proteins are potentially useful within the context of the present invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fed-batch, or continuous mode.

Following the polypeptide production phase, the polypeptide of interest is recovered from the culture medium using techniques which are well established in the art.

The polypeptide of interest preferably is recovered from the culture medium as a secreted polypeptide. As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A SEPHAROSE™ columns to remove contaminants such as IgG. A protease inhibitor such as phenyl methyl sulfonyl fluoride (PMSF) also may be useful to inhibit proteolytic degradation during purification.

The following examples are offered by way of illustration and not by way of limitation. The disclosures of all citations in the specification are expressly incorporated herein by reference.

EXAMPLES

Introduction

The following are general methods used in the Examples that follow.

Methods

DNA and Constructions. The chimeric gene encoding TNFR-IgG1 is described (Ashkenazi et al., (1991) Proc. Natl. Acad. Sci. 88:10535–10539). Site directed mutagenesis was carried out following the mismatched primer method of Kunkel, et al. (1985) Proc. Natl. Acad. Sci. 82:488–492) using the Muta-Gene M13 Kit (Bio-Rad Inc., Hercules, Calif.). Mutations were verified by dye terminator cycle sequencing using the automated ABI310 Genetic Analyzer (Applied Biosystems, Foster City, Calif.). For simplicity, the glycosylation mutants described in this paper are named using the single letter amino acid code with reference to the amino acid residue present at each of the four N-linked glycosylation sites at amino acid positions 14, 105, 111, and 248 (FIG. 1). Thus, the designation NNNN represents the fully glycosylated TNFR-IgG1, whereas NQNN indicates TNFR-IgG1 where glutamine replaced asparagine at the second glycosylation site (position 105). TNFR-IgG1 glycosylation variants were cloned into the expression vector pRK5 (Eaton et al., (1986) Biochem. 291:8343–8347), that enabled transient expression in the human embryonic kidney 293 cell line. The pRK5 chimeric transcription unit includes a cytomegalovirus (CMV) immediate early promoter and a simian virus 40 (SV-40) polyadenylation site. For expression in CHO cells, gene encoding TNFR-IgG1 variants were cloned into the closely related expression vector pSVI6B5 that differs from pRK5 in that transcription is directed by SV-40 promoter and enhancer elements rather than by the CMV promoter.

Cells and Transfections. 293 cells were cultured in 100 mm culture plates containing a mixture of Dulbecco's modified Eagles medium (DMEM) and Ham's F12 medium (F12) (Gibco BRL, Grand Island, N.Y.) supplemented with 10% whole fetal bovine serum (FBS) and incubated at 37° C. in an atmosphere containing 5% $CO_2$. Confluent plates of 293 cells were passaged at a ratio of 1:5; and were transfected at 60% confluency with plasmids containing TNFR-IgG1 glycosylation variants by the calcium phosphate method (Graham and Van Der Eb (1973) Virol. 52:456–467). For expression of TNFR-IgG1 variants in CHO cell lines, the genes encoding TNFR-IgG1 glycosylation site mutants were cloned into the pSVI6B5 expression vector. These plasmids were then co-transfected into CHO cells deficient in the production of dihydrofolate reductase (dhfr) along with a plasmid (pFD11) containing a cDNA encoding murine dhfr. The transfected cells were selected for the ability to grow in culture medium deficient in the production of glycine, hypoxanthine and thymidine. Resulting colonies were picked and then selected for growth in varying concentration of methotrexate. Stable cell lines expressing TNFR-IgG1 glycosylation site mutants were grown in 10 liter mini-fermentors, and growth conditioned cell culture medium was harvested for affinity purification (described below).

Metabolic Labeling and Immunoprecipitation. Two days post-transfection, the culture medium was removed from the transfected 293 cells and the cell monolayer washed twice with phosphate buffered saline (PBS). Cells were incubated in methionine and cysteine free DMEM and supplemented with ProMix 35S-Cell Labelling Mix (Amersham, Arlington Hts, Ill.) (100(Ci/mL). The cells were labeled 8–16 hours at 37° C. in an atmosphere of 5% CO2. After labeling, the cell supernatants were removed, centrifuged at 4000 rpm for 5 minutes, and 1 mL was aliquoted for immunoprecipitation experiments. The labeled cells were washed three times with PBS, lysed directly on the culture dishes with cell lysis buffer (PBS containing 3% NP-40), and centrifuged at 14,000×g for 5 minutes. The lysate was transferred to a fresh tube, and 200 μL was removed for immunoprecipitation. Immunoprecipitation of both supernatants and lysates was accomplished by addition of 30 μL of S. aureus Protein A (Pharmacia Inc., Piscataway, N.J.). After a short incubation period on ice (10–15 minutes) the Protein A/TNFR-IgG1 complexes were sedimented by centrifugation at 14,000×g for 1 minute, washed in wash buffer (PBS, 1% NP-40, 0.1% sodium dodecyl sulfate (SDS)), and resuspended in 2×sodium dodecyl sulfate polyacrylamide gel electrophoresis (SDS-PAGE) sample buffer containing 5% 2-mercaptoethanol (2-ME). The immunoprecipitated proteins were resolved by SDS-PAGE using 10% Tris-Glycine polyacrylamide gels (Novex, Inc., San Diego, Calif.). Proteins were visualized by autoradiography and mobilities were calculated with reference to $^{14}$C-Methylated Rainbow Colored Protein Molecular Weight Markers (Amersham, Arlington Heights, Ill.). Proteins were quantitated by densitometric scanning of autoradiographs using the Personal Densitometer (Molecular Dynamics, Sunnyvale, Calif.).

Pulse Chase Analysis. 48 hours post-transfection, cells were pulse-labeled with ProMix $^{35}$S-Cell Labeling Mix (500(Ci/mL) for 15 minutes. The labeling medium was then removed and the cell monolayer was washed at room temperature with PBS. Fresh medium (DMEM/F12+10% FBS) was then added, and cells were harvested at various time-points. For harvesting, plates were chilled on ice; supernatants were removed, and the cell monolayer was washed once with PBS. Cells were then lysed with 1 mL of lysis buffer. Lysate and supernatant samples were aliquoted and immunoprecipitated as described above.

Purification of TNFR-IgG glycosylation site mutants. Growth conditioned culture medium from cultures at 10 L CHO cells expressing TNFR-IgG1 glycosylation site mutations were purified by affinity chromatography on immobilized S. aureus protein A using a method described previously (Chamow et al. (1994) J. Immunol. 153:4268–4280). Four TNFR-IgG1 variants were purified: NNNN, NNQQ, NSNQ, and QSNQ. Briefly, purification was involved the following steps. (I) Prior to sample loading, the Protein A column was equilibrated with 20 mM Tris buffer, 15 mM NaCl (pH 7.4). After the growth conditioned cell culture medium was loaded onto the column, the column was sequentially washed with the following buffers: 20 mM Tris buffer, 150 mM NaCl (pH 7.4); 20 mM Tris buffer, 500 mM TMAC (pH 7.4); and 20 mM Tris buffer (pH 7.4). The glycosylation site mutants were eluted with 50 mM citric acid, 20% (w/v) glycerol (pH 3.0) and the elution pools were subsequently adjusted to pH 6.0 using 1.0 M sodium citrate. Finally, the eluates were buffer exchanged by gel filtration chromatography into PBS (pH 7.4). The purified mutants were analyzed using SDS-PAGE (12.5%) with Coomassie blue staining.

TNF binding assay. The binding of TNF to TNFR-IgG1 and TNFR-IgG1 glycosylation site mutants was determined using a competitive binding immunoassay similar to that described by Ashkenazi, et al. (1991) supra. Briefly, microliter plates were coated with affinity purified goat antibodies to human IgGFc domain. Purified TNFR-IgG1 or TNFR-IgG1 glycosylation site mutants were captured on the plates and then reacted with varying concentrations of unlabeled TNF (0.8 to 800 nM) and a fixed amount of ($^{125}$I)-labeled TNF (0.05 nM). After washing the amount of TNF remaining bound to the wells of the microtiter plates was determined with a gamma counter. Data were fit using a four parameter curve. The effective concentration of unlabeled TNF that resulted in halfmaximal (50%) binding of ($^{125}$I)-labeled TNF to TNFR-IgG1 glycosylation mutants was reported as $EC_{50}$ values.

Example 1

TNFR-IgG1 is a chimeric protein constructed by fusing the extracellular domain of the receptor for TNF alpha with sequences encoding the Fc domain and hinge region of IgG1 (Ashkenazi et al., (1991) supra). The chimeric protein (FIG. 1) contains four N-linked glycosylation sites: three located in the TNFR region (positions 14, 105, and 111) and one in the Fc domain (position 248). Previous studies have shown that TNFR-IgG1 is secreted as a homodimer, binds to TNF alpha with high affinity, and has potent anti-inflammatory activity in vivo.

Pulse-chase experiments were carried out to characterize the secretion efficiency of TNFR-IgG1. In these studies, 293 cells were transiently transfected with a calcium phosphate precipitated plasmid (pRK.TNFR-IgG1) and cultured for 2 days. The cells were pulse-labeled with ($^{35}$S)-methionine, and samples were collected at various time points. Immunoprecipitation studies (FIG. 2) indicated that TNFR-IgG1 first appeared in the cell culture medium approximately 1 hr after pulse labeling, and that the amount of secreted protein progressively increased over the entire 24 hr observation period. These studies also showed that a significant fraction of the TNFR-IgG1 synthesized during a 15 minute pulse labeling was retained inside the cells. Densitometric analysis of these data (FIG. 3A) demonstrated that only about 50% of the pulse-labeled protein was secreted from the cell during a 24 hr period, and that labeled precursor appeared to remain in a stable intracellular pool for more than 24 hr. The kinetics and pattern of secretion observed for TNFR-IgG1 were similar to those previously reported for two other secreted variants of membrane glycoproteins (Berman et al., (1989) J. Virol. 63: 3489–3498) suggesting that secretion of TNFR-IgG1 was similarly inefficient.

Endoglycosidase digestion and immunofluorescence studies similar to those described by Machamer and Rose (1988) J. Biol. Chem. 263:5955–5960) showed that the intracellular TNFR-IgG1 could be localized to the ER and was sensitive to endoglycosidase H digestion (endoH). These studies further showed that secreted TNFR-IgG1 was resistant to endo H digestion and sensitive to neuraminidase digestion. Together these results suggested that the intracellular TNFR-IgG1 accumulated in the endoplasmic reticulum (ER) and possessed the characteristic high mannose form of N-linked carbohydrate, whereas the secreted protein possessed terminal sialation acquired in the trans-Golgi apparatus (tGA).

Example 2

Deletion of glycosylation sites can impair secretion of TNFR-IgG1. To examine the effect of sequential deletion of glycosylation sites on the secretion of TNFR-IgG1, further experiments were carried out with a series of glycosylation mutants (Table 1).

TABLE 1

Summary of TNFR1-IgG1 Glycosylation Mutants

| Amino acid position | | | | |
|---|---|---|---|---|
| 14 | 105 | 111 | 248 | Secretion Efficiency |
| N | N | N | N | +++ |
| Q | N | N | N | ++ |
| N | Q | Q | N | + |
| N | N | N | Q | +++ |
| N | N | Q | N | + |
| N | Q | N | N | – |
| Q | N | N | Q | + |
| N | N | Q | Q | + |
| Q | Q | Q | N | +/– |
| Q | Q | Q | Q | – |
| N | S | N | N | +++ |
| N | N | S | N | + |
| N | D | D | N | + |
| N | K | K | N | ++ |
| N | S | S | N | – |
| N | R | R | N | + |
| N | T | T | N | +/– |
| Q | S | N | Q | – |
| N | D | D | Q | + |
| N | K | K | Q | ++ |

Figure 4A:
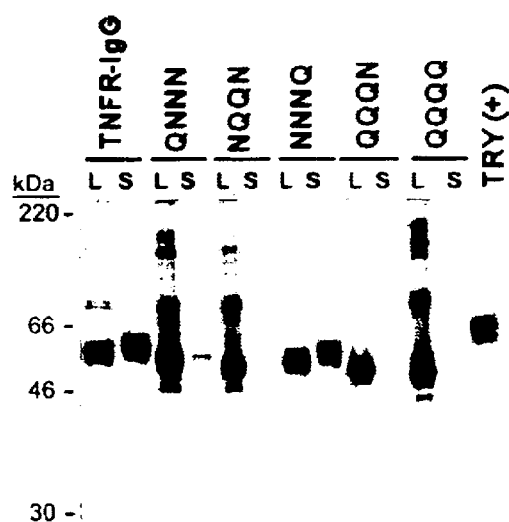
FIGS. 4A–4C. Immunoprecipitation of TNFR-IgG1 glycosylation mutants. Plasmids encoding either TNFR-IgG1 or TNFR-IgG glycosylation site mutants were transfected into 293 cells using calcium phosphate precipitated DNA. Two days post-transfection the culture, medium was removed and replaced (after washing two times) with methionine- and cysteine-free DMEM supplemented with ($^{35}$S)-labeled methionine and cysteine. Cells were labeled overnight at 37° C. (5% $CO_2$). Cell lysates and cell culture supernatants were precipitated by the addition of Protein A SEPHAROSE™. The Protein A:TNFR-IgG1 complexes were pelleted by centrifugation, washed repeatedly and eluted in SDS-PAGE sample buffer containing mercaptoethanol. The eluted protein was resolved on 10% SDS-PAGE gels and visualized by autoradiography. The glycosylation site mutants were examined in four separate experiments (FIGS. 4A–4D) where transiently expressed TNFR-IgG1 (TNFR-IgG1) expressed in 293 cells or a stable CHO cell line expressing TNFR-IgG (TRY+) were used as positive controls. Background binding was determined in experiments with cells transfected with thrombopoeitin (TPO–). The mobilities of molecular weight markers are indicated at the left margins.

In these studies, mutagenesis primers were designed to replace the codon specifying asparagine (N) in the N-linked carbohydrate attachment seqon, N-X-S/T, with codons specifying glutamine (Q). Because glycosylation sites 2 and 3 in TNFR-IgG1 are only a few amino acids apart (residues 105 and 111), a single mutageneis primer could be used to mutate both sites simultaneously. We found that all of the glycosylation mutants were expressed, but there were significant differences in secretion efficiency (FIG. 4A). Removal of the fourth glycosylation site (residue 248), located in the Fc domain of TNFR-IgG1 (NNNQ) had no effect on secretion, relative to wild type TNFR-IgG1 (NNNN). In contrast, removal of glycosylation sites 2 and 3 (NQQN) resulted in a nearly complete blockade of secretion. Deletion of the first glycosylation site (QNNN) also blocked secretion, however in this case secretion was approximately 35% of that seen with the fully glycosylated protein. Removal of the first three glycosylation sites (QQQN) completely inhibited secretion as did removal of all four glycosylation sites (QQQQ).

Figure 4B:
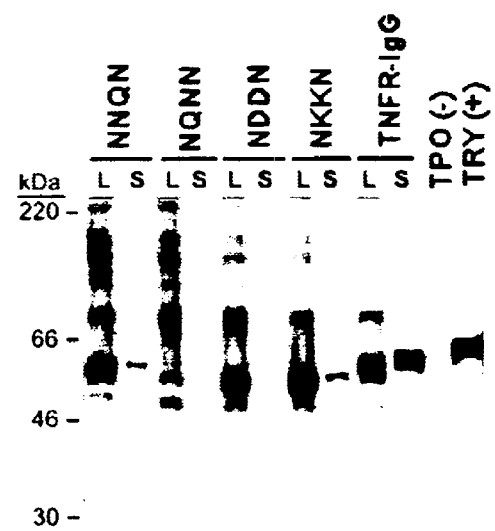

Further mutants were constructed (Table 1) to study, independently, the influence of glycosylation sites 2 and 3 on secretion. It was found that removal of glycosylation site 3 alone (NNQN) allowed for secretion at approximately 10% of level seen with the fully glycosylated protein, whereas deletion of glycosylation site 2 alone (NQNN) completely abolished secretion (FIG. 4B). Deletion of glycosylation sites 3 and 4 (NNQQ) resulted in a secretion efficiency (FIG. 4C) that was similar to the NNQN mutant but lower than the NNNQ mutant (FIG. 4B). Deletion of glycosylation sites 1 and 4 (QNNQ) resulted in significantly lower levels of secretion (FIG. 4C) than was observed with the QNNN and NNNQ mutants alone (FIG. 4A).

Example 3

Figure 4C:
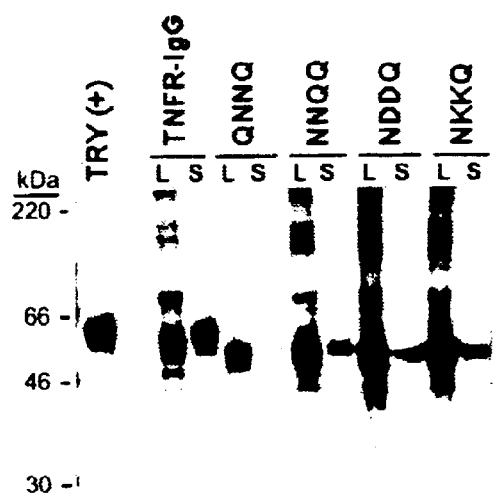
Figure 4D:
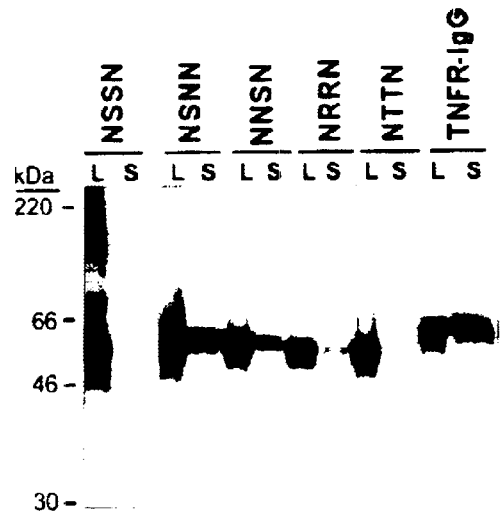

Nature of the amino acid side chain used to mutate N linked glycosylation site can effect secretion efficiency. Additional studies were carried out to determine if the nature of the amino acid side chain used for replacement of the N residue in the sequence creating an N-linked glycosylation site affected secretion efficiency. Each N-linked oligosaccharide chain can possess two to four sialic acid residues, depending on the antennarity of the high mannose precursor. We reasoned that replacement of N at N-linked glycosylation sites with charged residues (e.g. aspartic acid, glutamic acid, lysine, arginine) might have less effect on conformation than replacement with hydrophilic uncharged sidechains (e.g. glutamine, threonine, serine). We found that replacement of the N residues at glycosylation sites 2 and 3 with acidic, aspartic acid residues (NDDN) or basic, lysine residues (NKKN) allowed for better secretion (FIG. 4B) than the uncharged glutamine residues in the (NQQN) construct (FIG. 4A); however, the amount of protein secreted was far less than that observed with the wild-type TNFR-IgG1 protein. Replacement of asparagine at sites 2 and 3 with arginine (NRRN), also gave better secretion than the NQQN mutant, but the total amount of secreted protein appeared to be less compared to the NDDN or NKKN mutants (FIG. 4D).

We next considered the effect of uncharged, hydrophilic side-chains, serine and threonine, on the secretion efficiency of TNFR-IgG1. We found that replacement of glycosylation sites 2 and 3 with serine (NSSN) or threonine (NTTN), like the glutamine mutants (NQQN) completely inhibited secretion (FIG. 4D). However, single substitutions of serine for asparagine at glycosylation sites 2 and 3 with serine gave different results (FIG. 4D). The replacement of serine for asparagine at glycosylation site 2 (NSNN) allowed for better secretion than any of the other amino acid replacements examined at this position. In contrast, replacement of serine for asparagine at glycosylation site 3 (NNSN) resulted in secretion similar to that observed in the NNQN mutant (FIG. 4B).

Example 4

Triple deletion mutants. To investigate the effect of glycosylation site 4 in combination with sites 1–3, a series of mutants were constructed where three of the four glycosylation sites were deleted (Table 1). It was found that the NDDQ, the NKKQ, the NDDN and NKKN mutants were all secreted from transfected cells (FIG. 4C). However, in all four cases the amount of protein secreted was a small fraction (approximately 10%) of the amount secreted by fully glycosylated TNFR-IgG1. Thus, removal of glycosylation site 4 did not alter the secretion efficiency of variants where asparagine residues at glycosylation sites 2 and 3 were replaced by lysine or aspartic acid. A final mutant where three of the four glycosylation sites were deleted (QSNQ) was also examined (Table 1, FIG. 5). This variant accumulated intracellularly and was not secreted.

Example 5

Secretion efficiency of immunoadhesins can be improved by altering the signal sequence. Studies were performed to demonstrate that the yield and secretion efficiency of a representative immunoadhesin, TNFR-IgG1, from stably transfected CHO cells can be improved by replacement of the TNFR-IgG1 signal sequence with that of human tissue plasminogen activator (tPA). In these studies the signal sequences of herpes simplex virus type 1 glycoprotein D (HSV gD-1), Met-Gly-Gly-Thr-Ala-Ala-Arg-Leu-Gly-Ala-Val-Ile-Leu-Phe-Val-Val-Ile-Val-Gly-Leu-His-Gly-Val-Arg-Gly (SEQ ID NO: 9), recombinant human DNase, Met-Arg-Gly-Lys-Leu-Leu-Gly-Ala-Leu-Leu-Ala-Leu-Ala-Ala-Leu-Leu-Gln-Gly-Ala-Val-Ser (SEQ ID NO: 10), HER-2, Met-Gly-Trp-Ser-Cys-Ile-Ile-Leu-Phe-Leu-Val-Ala-Thr-Ala-Thr-Gly-Val-His-Ser (SEQ ID NO: 11), TNFR, Met-Gly-Leu-Ser-Thr-Val-Pro-Asp-Leu-Leu-Leu-Pro-Leu-Val-Leu-Leu-Glu-Leu-Leu-Val-Gly-Ile-Tyr-Pro-Ser-Gly-Val-Ile-Gly (SEQ ID NO: 2) (Ashkenazi et al., (1991) Proc. Natl. Acad. Sci. 88:10535–10539), and t-PA (SEQ ID NO: 1) were operably linked to the nucleic acid sequence encoding TNFR1-IgG1 and the secretion kinetics were followed. The results indicated an increase in amount of TNFR-IgG1 that could be recovered from the supernatant as well as an improvement in the secretion kinetics (2 hrs and 24 hrs).

Figure 3A:
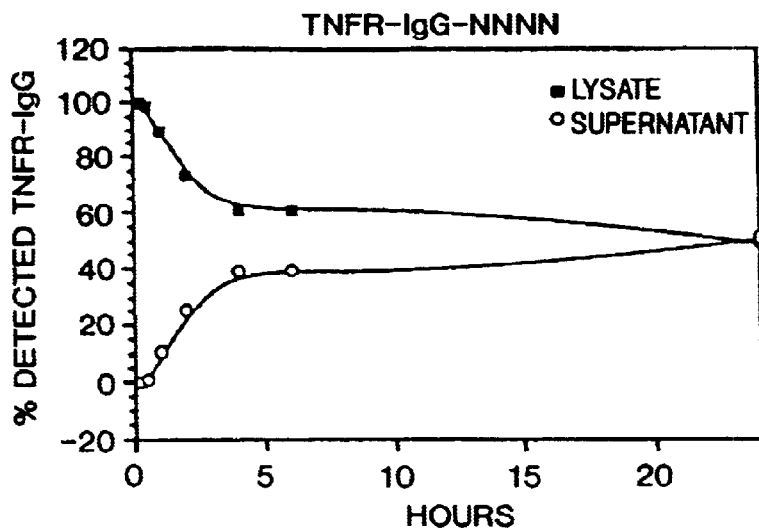
FIGS. 3A–3F. Secretion kinetics of TNFR-IgG1 signal sequence and glycosylation mutants. Plasmids encoding fully glycosylated (FIG. 3A) or mutated forms of TNFR-IgG1 (FIGS. 3B–3F) were transfected into 293 cells and analyzed by pulse-chase analysis as described in FIG. 2. Autoradiographs were analyzed with a scanning densitometer and the optical density values for supernatants (o) and cell lysates (■) were normalized and plotted as a function of time (0–24 hr). The glycosylation site mutants are identified using the single letter amino acid code with reference to the amino acid residue present at each of the four N-linked glycosylation sites (amino acid positions 14, 105, 11 1, and 248). Thus, the designation NNNN represents the wild type TNFR-IgG1, whereas NQNN indicates TNFR-IgG1 where glutamine replaced asparagine at the second glycosylation site (position 105).
Figure 3B:
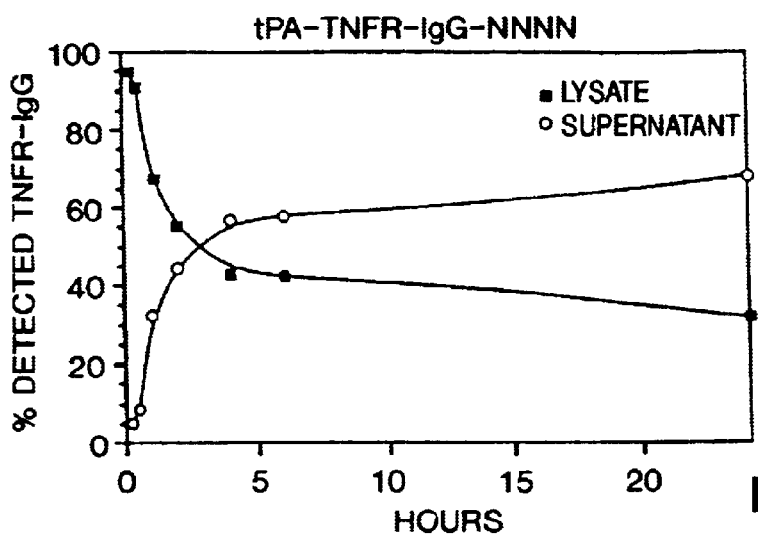

To determine whether the tPA signal/pro-sequence improved yield by increasing the efficiency of intracellular transport, a plasmid (pRK.tPA-TNFR-IgG1) was constructed for transient transfection studies in 293 cells. Pulse-chase studies (FIG. 2, FIGS. 3A and B) showed that replacement of the TNFR signal sequence with the tPA signal/pro sequence resulted in a significant improvement in secretion efficiency. Thus, after 24 hours, approximately 70–80% of the pulse-labeled TNFR-IgG1 was secreted into the cell culture medium when the tPA signal/pro sequence was included, whereas only 50–60% of the protein was secreted using the wild-type TNFR signal sequence. The increased efficiency of secretion achieved with the tPA signal/pro sequence was apparent from the kinetics of secretion of TNFR-IgG1 (FIG. 2, FIGS. 3A and B). When the TNF signal/pro sequence was used, only 40% of the pulse-labeled TNFR-IgG1 was secreted in 2–4 hr after pulse labeling. However when the TNF signal sequence was replace with the tPA signal/pro sequence approximately 60% of the TNFR-IgG synthesized with the TNFR signal sequence was secreted in this time frame.

Figure 5A:
FIGS. 5A and 5B. Effect of signal sequence replacement on the secretion of TNFR-IgG1 glycosylation site mutants. Plasmids encoding TNFR-IgG1 glycosylation site mutants containing the tPA signal/pro sequence (tPA) (SEQ ID NO: 1) or the TNFR signal sequence (TNFR) (SEQ ID NO: 2) were transfected into 293 cells, metabolically labeled with ($^{35}$S) methionine and cysteine, and immunoprecipitated from cell culture supernatants (S) or cell lysates (L) by the addition of Protein A SEPHAROSE™ as described in FIG. 4. The Protein A:TNFR-IgG1 complexes were pelleted by centrifugation, resolved by SDS-PAGE, and visualized by autoradiography. The mobilities of molecular weight markers are indicated at the left margins.

Studies of the biosynthesis of tPA have shown that the N terminal processing of tPA is complex and involves co-translational cleavage of a 21 amino acid signal sequence, post-translation cleavage of an 11 amino acid pro-sequence at a furin cleavage site, and extracellular cleavage of a 3 amino acid, N-terminal peptide by an undefined exopeptidase (FIG. 1). This complex strategy for N terminal processing of TNFR-IgG1 mutants is supported by our results showing that intracellular TNFR-IgG1 variants possessing the tPA signal/pro sequence possessed higher molecular weights than the corresponding secreted proteins (FIG. 5A). Since furin is known to be localized in the trans-GA, the pro-sequence would not be expected to be removed until the tPA-TNFR precursor has been transported from the ER to the trans-GA. Endoglycosidase digestion studies and immunofluorescence studies have provided data consistent with an ER localization of intracellular variants of tPA.TNFR-IgG1.

Example 6

Secretion efficiency of glycosylation site mutants can be improved by altering the signal sequence. To determine whether signal sequence exchange could improve the secretion efficiency of the TNFR-IgG1 glycosylation site mutants described in FIG. 4, the TNFR signal sequence was deleted and replaced by the tPA signal/pro sequence. It was found (Table 2, FIG. 5) that the signal sequence exchange resulted in a marked increase in secretion efficiency of these glycosylation site mutants.

TABLE 2

Effect of tPA Signal Sequence or Secretion of TNFR1-IgG1 Glycosylation Mutants

| Mutant | % Secretion Efficiency* | | EC50 for TNF Binding‡ |
|---|---|---|---|
| | TNFR.ss | tPA.ss | (nM) |
| NNNN | 50 | 70 | 6.66 +/− 0.73 |
| NNQQ | 20 | 70 | 4.74 +/− 0.48 |
| NSNQ | <5 | 60 | 6.94 +/− 0.83 |
| NKKQ | 10 | 40 | ND |
| QSNQ | <5 | 65 | 2.34 +/− 0.22 |
| QQQQ | <5 | <5 | ND |

*Data represent results from pulse-chase experiments (e.g. FIG. 3) where the percentage of pulse-labeled protein secreted in a 24 hr period was measured by scanning densitometry.
‡Data represent EC50 values for the displacement of ($^{125}$I)-labeled TNF by TNFR-IgG1 glycosylation site mutants (FIG. 7).

Figure 3C:
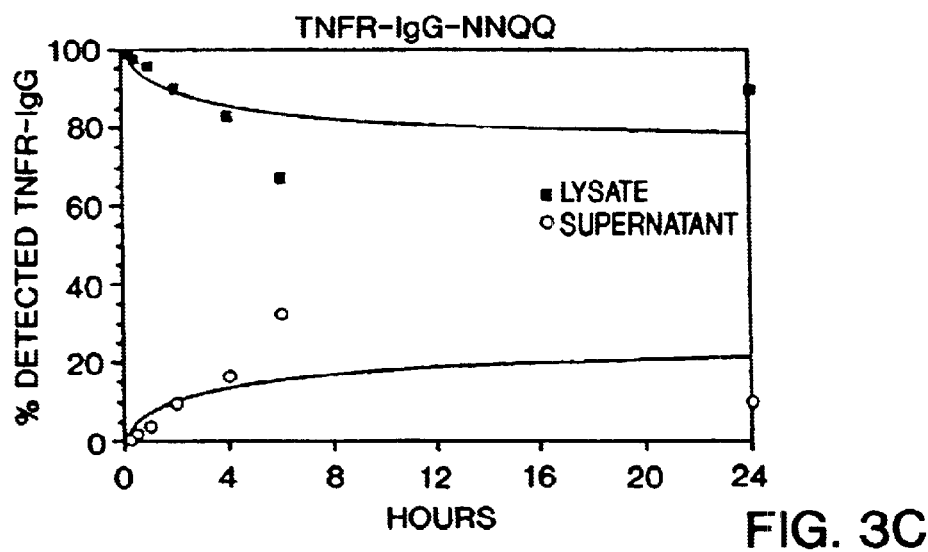
Figure 3A:
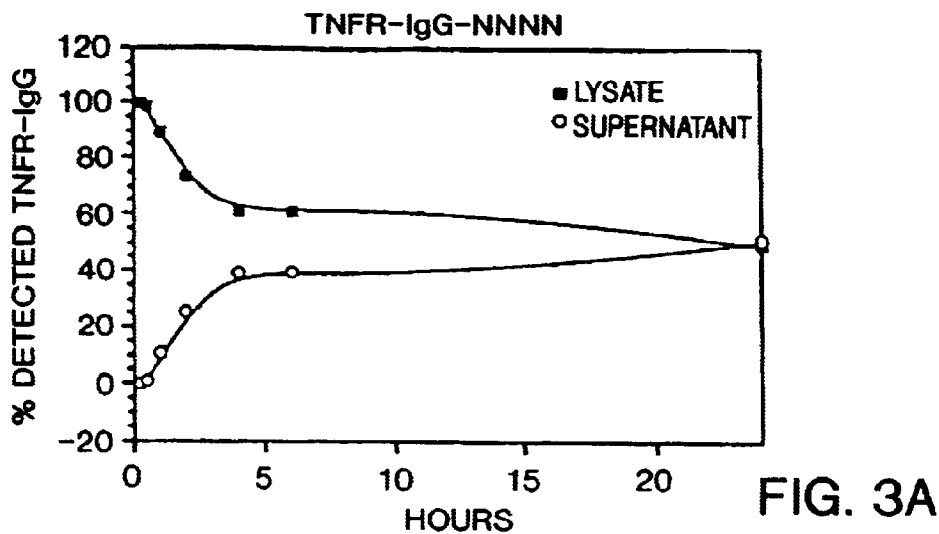
Figure 3B:
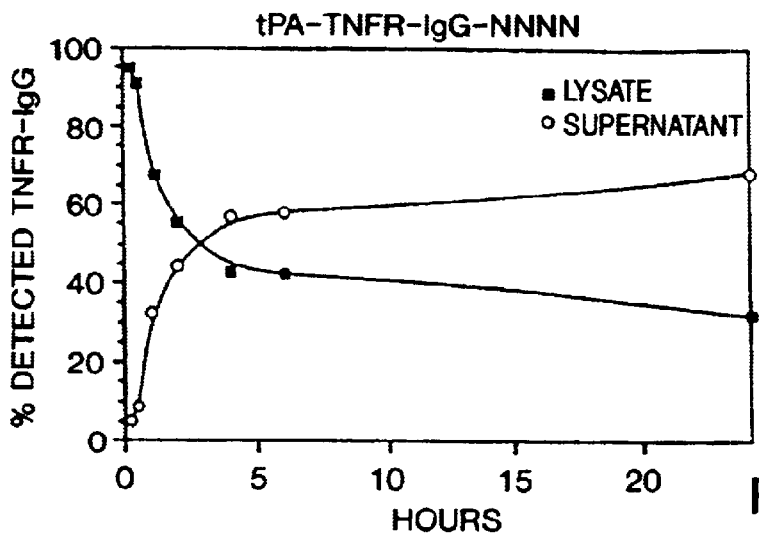
Figure 3C:
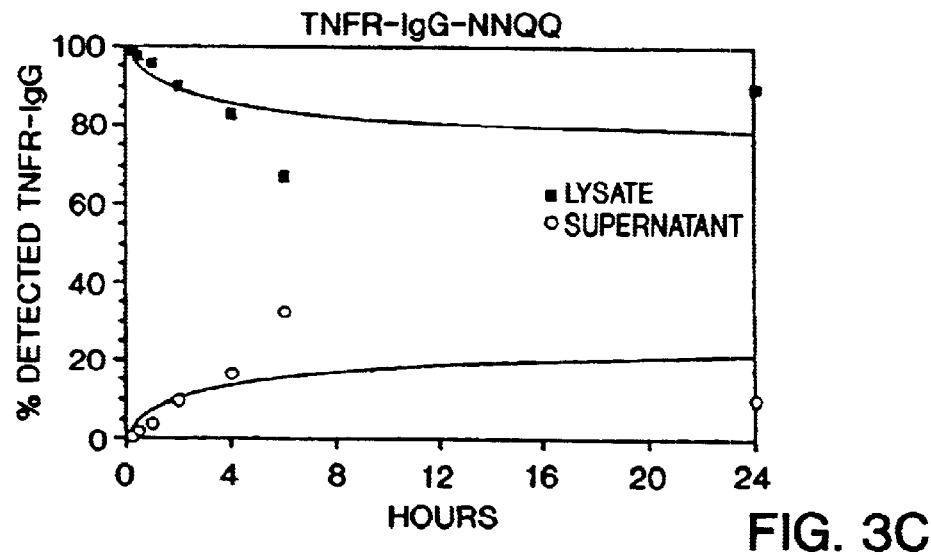
Figure 5B:
Figure 3D:
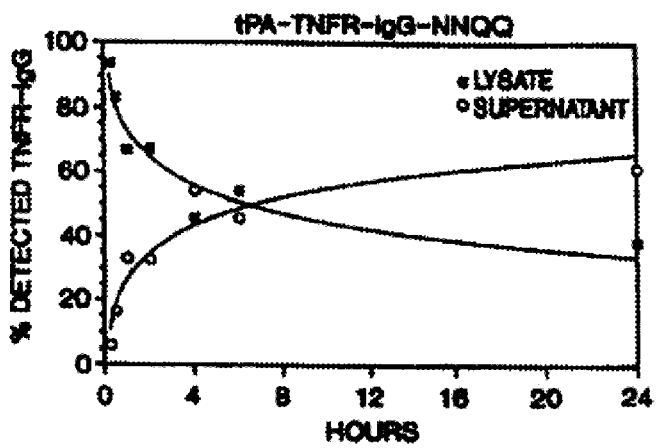
Figure 3E:
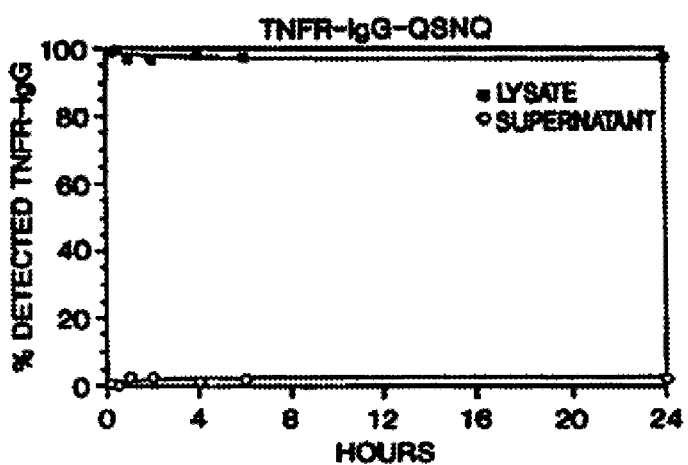
Figure 3F:
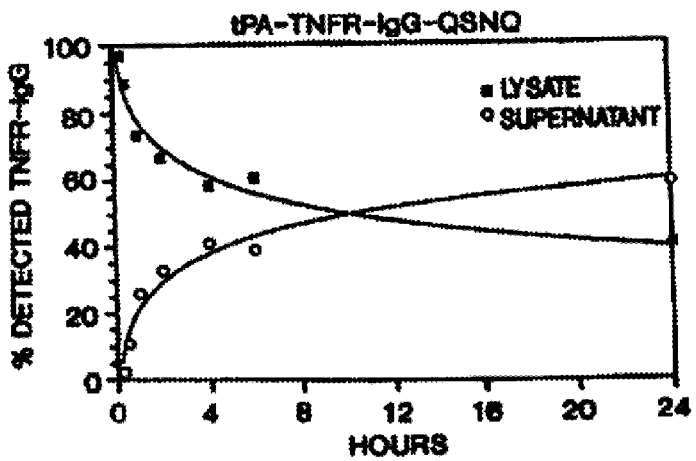
Figure 4A:
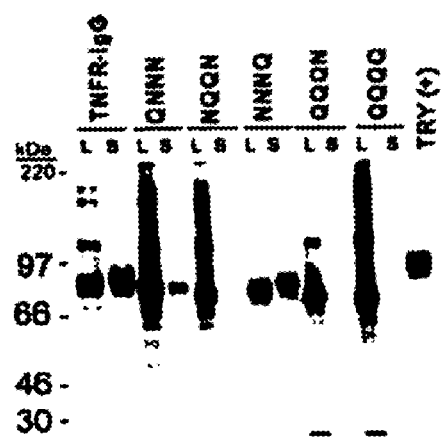
Figure 4B:
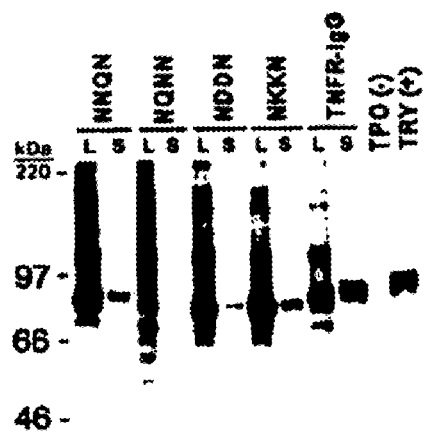
Figure 4C:
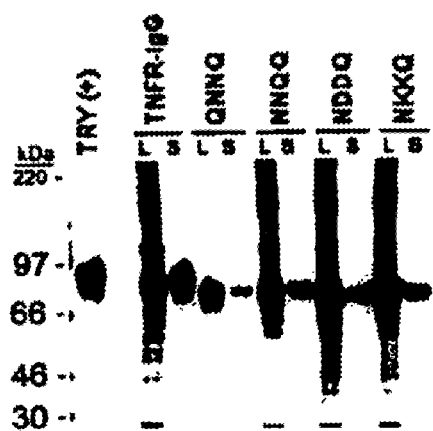
Figure 4D:
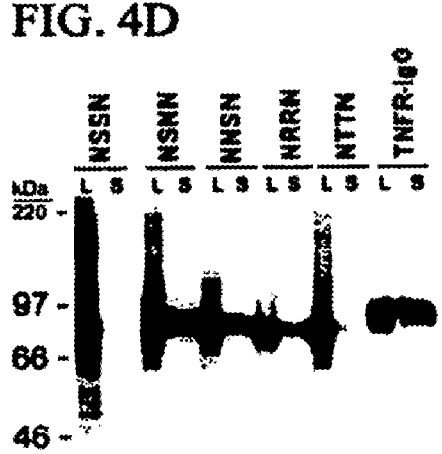

For example, only 10–20% of the NNQQ mutant was secreted using the TNFR signal sequence, whereas 60–70% of the NNQQ mutant containing the tPA signal/pro sequence was secreted (FIGS. 3C and D, FIG. 5). Similarly, little or none of the QSNQ mutant was secreted containing the TNFR signal sequence, but approximately 60% was secreted from the tPA signal/pro sequence containing variant (FIGS. 3E and F, FIG. 5). Similar improvements in secretion efficiency were observed for the NKKQ and NSNQ mutants (FIG. 5). Densitometric analysis of pulse chase experiments (FIG. 3) showed that attachment of the tPA signal/pro sequence accelerated the kinetics of intracellular transport as well as increasing the total amount of secreted protein. Although replacement of the tPA/pro sequence could overcome the blockade of protein secretion for many of the glycosylation mutants, this strategy was not effective for the fully glycosylated QQQQ glycosylation site mutant (FIG. 5).

Example 7

Figure 6:
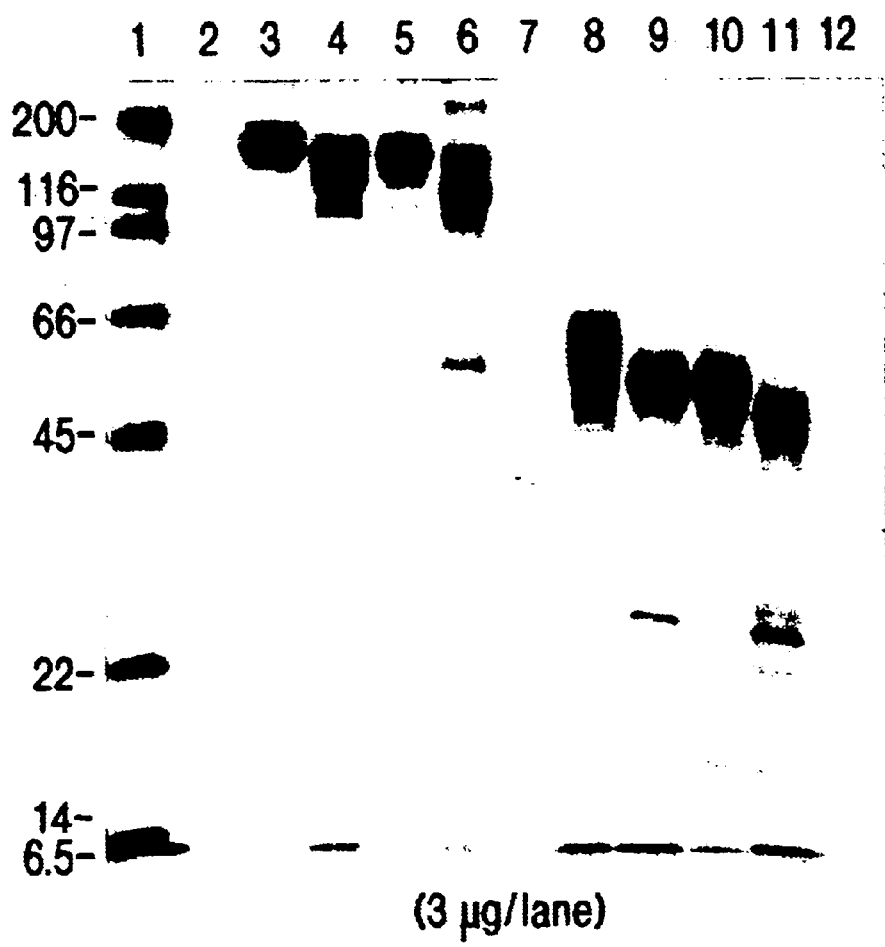
FIG. 6. Characterization of TNFR-IgG1 glycosylation mutants purified for receptor binding studies. TNFR-IgG1 glycosylation site mutants were purified by protein A affinity chromatography from growth conditioned cell culture supernatants of stabile transfected CHO cells. The purified proteins were treated with SDS-PAGE sample buffer with— (lanes 8–12) or without (lanes 3–6) added 2-mercaptoethanol and resolved by SDS-PAGE. The resulting gel was stained with Coomassi blue. Each lane contained 3 ug of purified protein. Lanes 3 and 8 contained fully glycosylated TNFR-IgG1; lanes 4 and 9 contained the NNQQ glycosylation site mutant; lanes 5 and 10 contained the NSNQ glycosylation site mutant; lanes 6 and 11 contained the QSNQ glycosylation site mutant. Lane 1 contained molecular weight standards (indicated at left margin), lanes 2, 7, and 12 contained sample buffer alone.
Figure 7A:
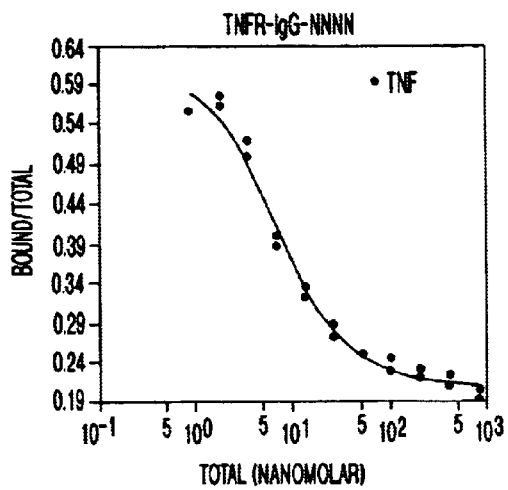
FIGS. 7A–7D. Competitive binding of ($^{125}$I)-labeled TNF to TNFR-IgG1 glycosylation mutants. Purified TNFR-IgG1 and TNFR-IgG1 glycosylation site mutants were captured onto micotiter plates coated with affinity purified goat antibodies to human IgG Fc domain. The captured receptor chimeras were reacted with ($^{125}$I)-labeled TNF along with varying concentrations of unlabeled TNF. The binding of TNF to fully glycosylated TNFR-IgG1 is shown in FIG. 7A; binding to the NNQQ glycosylation mutant is shown in FIG. 7B; binding to the NSNQ glycosylation mutant is shown in FIG. 7C; and binding to the QSNQ glycosylation mutant is shown in FIG. 7D.
Figure 7B:
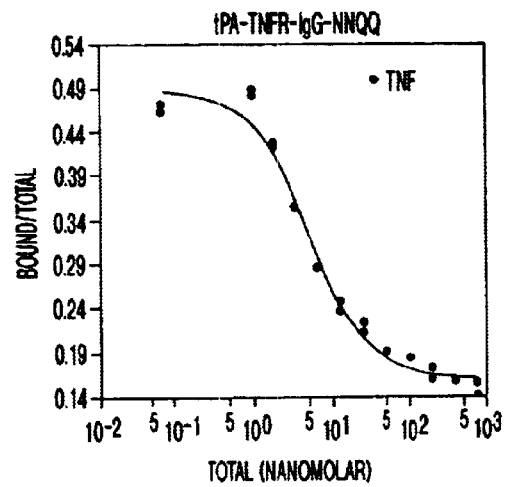
Figure 7C:
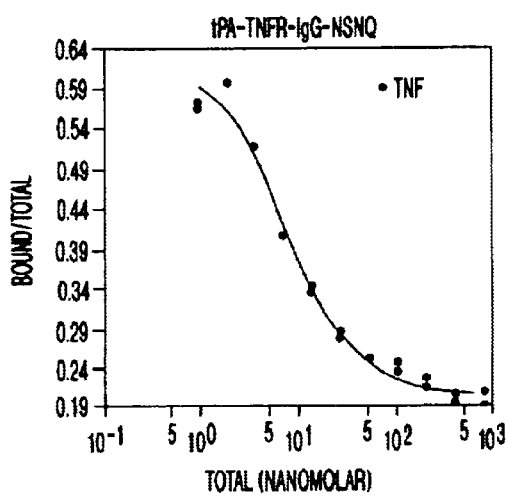
Figure 7D:
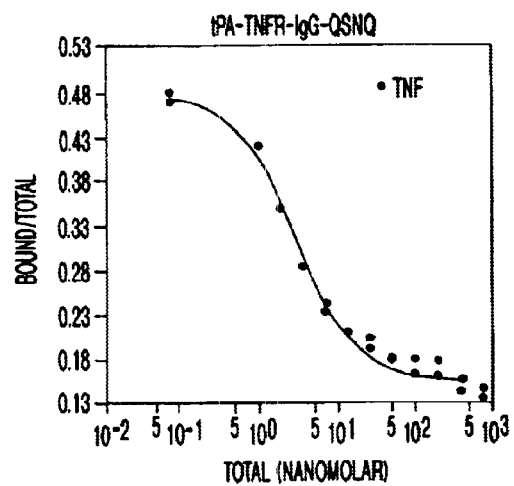

Structure and TNF binding activity of TNFR-IgG1 glycosylation mutants. Although the signal sequence exchange strategy described above provided a method that allowed for the secretion of TNFR-IgG1 glycosylation site mutants, we wondered whether the secreted proteins were properly folded. To answer this question, stable CHO cell lines, expressing several of the TNFR-IgG1 glycosylation mutants, were constructed in order to produce sufficient quantities for ligand binding studies. Recombinant proteins representing the NNQQ, NSNQ, and QSNQ mutants were purified from growth conditioned cell culture medium using protein A affinity chromatography. It was found (FIG. 6) that the glycosylation site mutants, like TNFR-IgG1, associated to form covalent disulfide bonded dimers that were stable in SDS and could be dissociated by the addition of reducing agents (e.g. 2-mercaptoethanol). As expected, the molecular mass of the glycosylation variants correlated with the number of intact glycosylation sites. Thus the variants with two glycosylation sites deleted (NNQQ and NSNQ) were smaller in molecular weight than the wild type (NNNN) proteins and larger in molecular mass than the QSNQ variant the possessed only one glycosylation site.

TNF binding studies were carried out to determine whether the secreted glycosylation variants were folded into a functionally relevant conformation. For this purpose, the three glycosylation mutants illustrated in FIG. 6 were evaluated in a binding assay. (FIG. 7) using ($^{125}$I)-labeled TNF by a method similar to that described by Ashkenazi et al. All three mutants bound the ($^{125}$I)-labeled TNF with $EC_{50}$ values (Table 2) comparable to that observed for fully glycosylated TNFR-IgG1. These studies suggested that neither glycosylation sites nor the tPA signal/pro sequence affected the interaction of TNFR-IgG1 with it's ligand.

Example 8

Figure 8A:
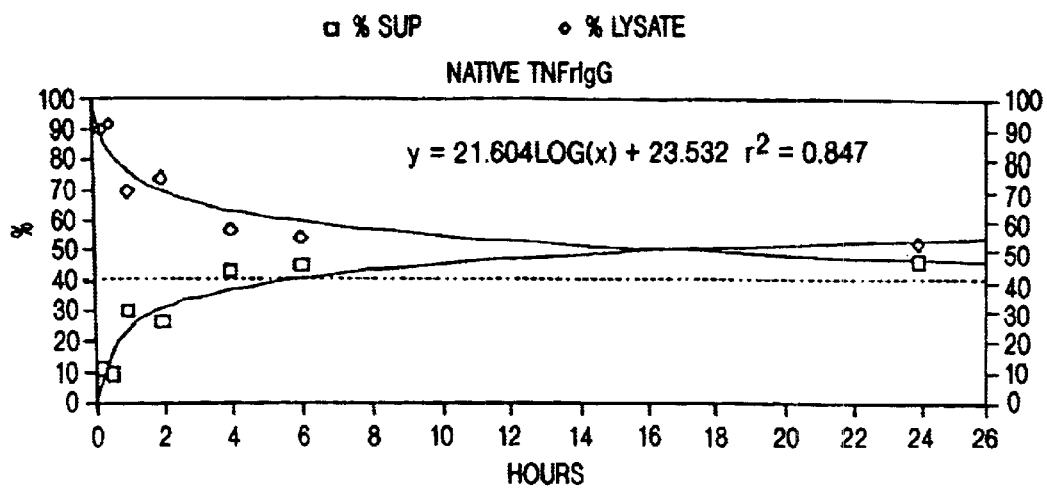
FIGS. 8A–C. Secretion kinetics of TNFR-IgG1 signal sequence variants. Plasmids encoding TNFR1-IgG1 utilizing the signal sequence of TNFR1 (SEQ ID NO: 2)(FIG. 8A), the signal-pro sequence of tPA (SEQ ID NO: 1) (FIG. 8B) or the signal sequence of TNFR1 (SEQ ID NO: 2) and a pro-sequence (SEQ ID NO: 7) of human t-PA (SEQ ID NO: 8) (FIG. 8C) were transfected into CHO cells and analyzed by pulse-chase analysis as described in FIG. 2. Autoradiographs were analyzed with a scanning densitometer and the optical density values for supernatants (□) and cell lysates (◇) were normalized and plotted as a function of time (0–24 hr).
Figure 8B:
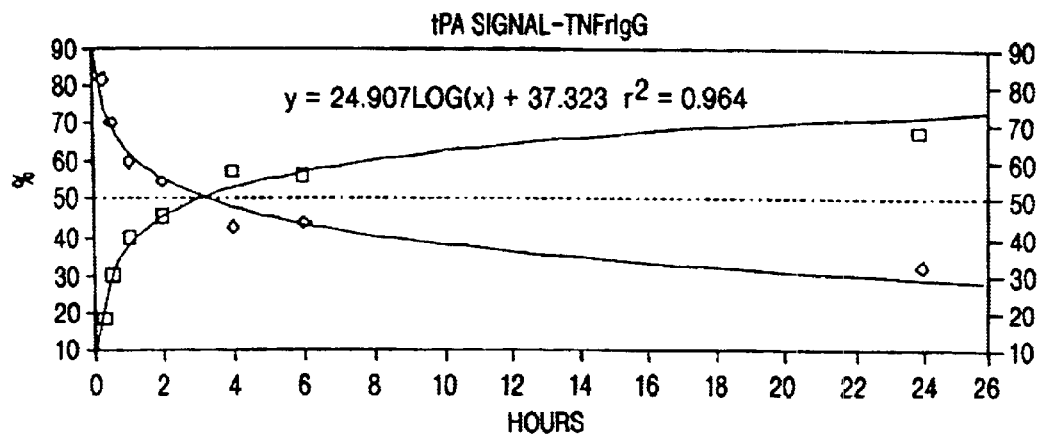
Figure 8C:
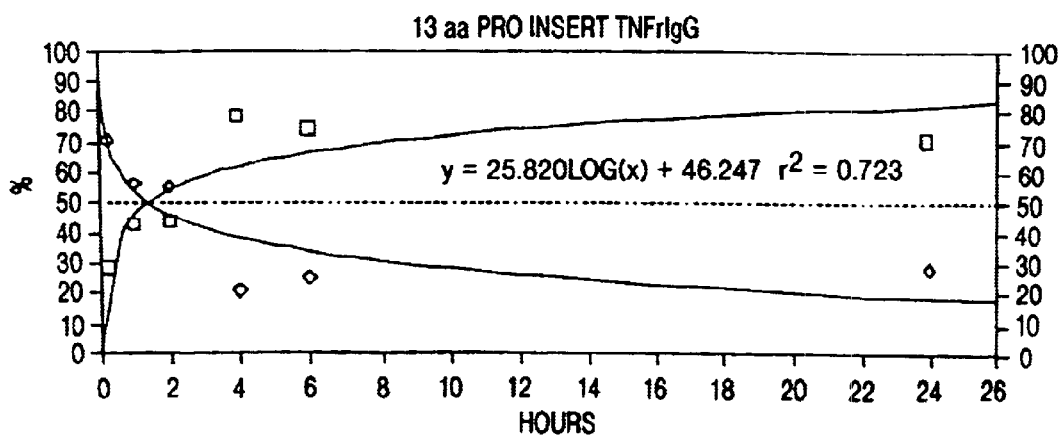

To determine the influence of the tPA propeptide on secretion kinetics of tPA/TNFR-IgG1 a construct was generated containing the 29aa TNFR signal sequence (SEQ ID NO: 2) and a 13 amino acid t-PA propeptide (SEQ ID NO: 7) having the sequence Met-Gly-Leu-Ser-Thr-Val-Pro-Asp-Leu-Leu-Leu-Pro-Leu-Val-Leu-Leu-Glu-Leu-Leu-Val-Gly-Ile-Tyr-Pro-Ser-Gly-Val-Ile-Gly-Ser-Gln-Glu-Ile-His-Ala-Arg-Phe-Arg-Arg-Gly-Ala-Arg (SEQ ID NO: 8) was prepared. From RIP experiments SEQ ID NO: 8 was shown to have similar $t^{1/2}$max and percent secretion at 24 hours to that of tPA/TNFR-IgG1 (FIGS. 8A–C). Endo H digest also reveal similar secretion kinetics to that of tPA/TNFR-IgG1, where approximately ⅓ of the lysate is endo H resistant between 10 and 30 minutes and is probably secreted within 30 minutes, as opposed to the wild type TNFr-IgG in which very little of the lysate is Endo H resistant and the band does not decrease over time. This evidence strongly indicates that the decrease in $t^{1/2}$max and percent secretion at 24 hours for tPA/TNFR-IgG1 is due to the presence of the 13 amino acid propeptide. This is supported by transient expression data, wherein 14 yields similar total expression as well as specific productivity.

What is claimed is:

1. A DNA construct comprising a first DNA segment comprising a nucleic acid sequence that encodes mammalian t-PA pro-sequence operatively linked to a nucleic acid sequence that encodes a pre-sequence other than a mammalian t-PA pre-sequence; and a second DNA segment operably linked to the first DNA segment, wherein the second DNA segment encodes a heterologous glycoprotein.

2. The DNA construct of claim 1, wherein the heterologous glycoprotein is an immunoadhesin.

3. The DNA construct of claim 2, wherein the immunoadhesin is a TNF receptor immunoadhesin.

4. The DNA construct of claim 3, wherein the TNF receptor immunoadhesin is TNFR1-IgG1.

5. The DNA construct of claim 1, wherein the heterologous glycoprotein is a glycosylation site deletion variant glycoprotein.

6. The DNA construct of claim 1, wherein the mammalian t-PA pro-sequence is operably linked to a pre-sequence associated with the native heterologous polypeptide.

7. The DNA construct of claim 6, wherein the heterologous glycoprotein is a TNF receptor immunoadhesin and the pre-sequence is a pre-sequence of a mammalian TNF receptor.

8. The DNA construct of claim 7, wherein the mammalian t-PA pro-sequence is SEQ ID NO. 7.

9. The DNA construct of claim 8, wherein the pre-sequence is SEQ ID NO. 8.

10. The DNA construct of claim 9, wherein the TNF receptor immunoadhesin is TNFR1-IgG1.

11. An expression vector comprising the DNA construct of claim 1.

12. A transformed eukaryotic cell comprising the expression vector of claim 11.

13. A method of producing a glycoprotein comprising:

(a) culturing a eukaryotic cell comprising an expression vector comprising a first DNA segment comprising a nucleic acid sequence that encodes mammalian t-PA pro-sequence operatively linked to a nucleic acid sequence that encodes a pre-sequence other than a mammalian t-PA pre-sequence and a second DNA segment operably linked to the first DNA segment, wherein the second DNA segment encodes a heterologous glycoprotein;

(b) recovering the glycoprotein from the cell culture.

* * * * *

UNITED STATES PATENT AND TRADEMARK OFFICE
CERTIFICATE OF CORRECTION

PATENT NO.       : 6,693,181 B2
APPLICATION NO.  : 09/291925
DATED            : February 17, 2004
INVENTOR(S)      : Ashkenazi et al.

It is certified that error appears in the above-identified patent and that said Letters Patent is hereby corrected as shown below:

Delete Drawings, Sheet 4 of 9: and replace with attached Sheet 4 of 9

Delete Drawings, Sheet 5 of 9: and replace with attached Sheet 5 of 9

Column 30, lines 15-16, claim 9: "the pre-sequence is SEQ ID" should read --the pre-sequence is the pre-sequence of SEQ ID--

Signed and Sealed this

Fourth Day of March, 2008

JON W. DUDAS
*Director of the United States Patent and Trademark Office*

SEQUENCE LISTING

<160> NUMBER OF SEQ ID NOS: 13

<210> SEQ ID NO 1
<211> LENGTH: 35
<212> TYPE: PRT
<213> ORGANISM: Homo sapiens

<400> SEQUENCE: 1

Met Asp Ala Met Leu Arg Gly Leu Cys Cys Val Leu Leu Leu Cys
 1               5                  10                  15

Gly Ala Val Phe Val Ser Pro Ser Gln Glu Ile His Ala Arg Phe
                20                  25                  30

Arg Arg Gly Ala Arg
                35

<210> SEQ ID NO 2
<211> LENGTH: 29
<212> TYPE: PRT
<213> ORGANISM: Homo sapiens

<400> SEQUENCE: 2

Met Gly Leu Ser Thr Val Pro Asp Leu Leu Pro Leu Val Leu
 1               5                  10                  15

Leu Glu Leu Leu Val Gly Ile Tyr Pro Ser Gly Val Ile Gly
                20                  25

<210> SEQ ID NO 3
<211> LENGTH: 21
<212> TYPE: PRT
<213> ORGANISM: Homo sapiens

<400> SEQUENCE: 3

Met Asp Ala Met Leu Arg Gly Leu Cys Cys Val Leu Leu Leu Cys
 1               5                  10                  15

Gly Ala Val Phe Val Ser
                20

<210> SEQ ID NO 4
<211> LENGTH: 11
<212> TYPE: PRT
<213> ORGANISM: Homo sapiens

<400> SEQUENCE: 4

Pro Ser Gln Glu Ile His Ala Arg Phe Arg Arg
 1               5                  10

<210> SEQ ID NO 5
<211> LENGTH: 14
<212> TYPE: PRT
<213> ORGANISM: Homo sapiens

<400> SEQUENCE: 5

Pro Ser Gln Glu Ile His Ala Arg Phe Arg Arg Gly Ala Arg
 1               5                  10

<210> SEQ ID NO 6
<211> LENGTH: 32
<212> TYPE: PRT
<213> ORGANISM: Homo sapiens

<400> SEQUENCE: 6

Met Asp Ala Met Leu Arg Gly Leu Cys Cys Val Leu Leu Leu Cys
 1               5                  10                  15

Gly Ala Val Phe Val Ser Pro Ser Gln Glu Ile His Ala Arg Phe
                20                  25                  30

Arg Arg

<210> SEQ ID NO 7
<211> LENGTH: 13
<212> TYPE: PRT
<213> ORGANISM: Homo sapiens

<400> SEQUENCE: 7

-continued

Ser Gln Glu Ile His Ala Arg Phe Arg Arg Gly Ala Arg
 1               5                  10

<210> SEQ ID NO 8
<211> LENGTH: 42
<212> TYPE: PRT
<213> ORGANISM: Artificial sequence
<220> FEATURE:
<223> OTHER INFORMATION: combination of two human sequences

<400> SEQUENCE: 8

Met Gly Leu Ser Thr Val Pro Asp Leu Leu Pro Leu Val Leu
 1               5                  10                  15

Leu Glu Leu Leu Val Gly Ile Tyr Pro Ser Gly Val Ile Gly Ser
                20                  25                  30

Gln Glu Ile His Ala Arg Phe Arg Arg Gly Ala Arg
                35                  40

<210> SEQ ID NO 9
<211> LENGTH: 25
<212> TYPE: PRT
<213> ORGANISM: Herpesvirus

<400> SEQUENCE: 9

Met Gly Gly Thr Ala Ala Arg Leu Gly Ala Val Ile Leu Phe Val
 1               5                  10                  15

Val Ile Val Gly Leu His Gly Val Arg Gly
                20                  25

<210> SEQ ID NO 10
<211> LENGTH: 21
<212> TYPE: PRT
<213> ORGANISM: Homo sapiens

<400> SEQUENCE: 10

Met Arg Gly Lys Leu Leu Gly Ala Leu Leu Ala Leu Ala Ala Leu
 1               5                  10                  15

Leu Gln Gly Ala Val Ser
                20

<210> SEQ ID NO 11
<211> LENGTH: 19
<212> TYPE: PRT
<213> ORGANISM: Homo sapiens

<400> SEQUENCE: 11

Met Gly Trp Ser Cys Ile Ile Leu Phe Leu Val Ala Thr Ala Thr
 1               5                  10                  15

Gly Val His Ser

<210> SEQ ID NO 12
<211> LENGTH: 22
<212> TYPE: PRT
<213> ORGANISM: Homo sapiens

<400> SEQUENCE: 12

Met Asp Ala Met Leu Arg Gly Leu Cys Cys Val Leu Leu Leu Cys
 1               5                  10                  15

Gly Ala Val Phe Val Ser Pro
                20

```
<210> SEQ ID NO 13
<211> LENGTH: 10
<212> TYPE: PRT
<213> ORGANISM: Homo sapiens

<400> SEQUENCE: 13

Ser Gln Glu Ile His Ala Arg Phe Arg Arg
 1               5                  10
```